(12) United States Patent
Siegel et al.

(10) Patent No.: US 10,279,155 B1
(45) Date of Patent: May 7, 2019

(54) METHODS AND SYSTEMS FOR BATHING NOSE AND SINUS PASSAGES

(71) Applicant: Michael B. Siegel, Rockville, MD (US)

(72) Inventors: Michael B. Siegel, Rockville, MD (US); Jesse C. Bunch, Silver Spring, MD (US); Justin S. Siegel, Rockville, MD (US)

(73) Assignee: Michael B. Siegel, Rockville, MD (US)

( * ) Notice: Subject to any disclaimer, the term of this patent is extended or adjusted under 35 U.S.C. 154(b) by 801 days.

(21) Appl. No.: 14/070,815

(22) Filed: Nov. 4, 2013

Related U.S. Application Data

(60) Provisional application No. 61/852,192, filed on Mar. 16, 2013, provisional application No. 61/796,105, filed on Nov. 2, 2012.

(51) Int. Cl.
*G01C 9/06* (2006.01)
*A61M 31/00* (2006.01)

(52) U.S. Cl.
CPC ............... *A61M 31/00* (2013.01); *G01C 9/06* (2013.01)

(58) Field of Classification Search
CPC .......... A01N 43/56; A61M 2210/0618; A61M 15/08; A61M 15/085; A61M 16/0463; A61M 16/0475
See application file for complete search history.

(56) References Cited

U.S. PATENT DOCUMENTS

| | | | |
|---|---|---|---|
| 3,847,145 A | 11/1974 | Grossan | |
| 3,909,004 A | 9/1975 | Vella | |
| 4,350,159 A * | 9/1982 | Gouda | A61B 90/11 606/129 |
| 4,528,990 A | 7/1985 | Knowles | |
| 4,777,965 A | 10/1988 | Allison et al. | |
| 4,802,485 A * | 2/1989 | Bowers | A61B 5/0816 600/324 |
| 4,928,709 A | 5/1990 | Allison et al. | |
| 4,934,706 A | 6/1990 | Marshall | |
| 5,176,515 A * | 1/1993 | Andrews | A61C 19/045 433/24 |
| 5,330,485 A * | 7/1994 | Clayman | A61B 90/11 606/1 |

(Continued)

FOREIGN PATENT DOCUMENTS

EP 0319501 A2 6/1989

*Primary Examiner* — Bhisma Mehta
*Assistant Examiner* — Matthew A Engel
(74) *Attorney, Agent, or Firm* — Edell, Shapiro & Finnan, LLC

(57) ABSTRACT

A system and method for delivering a bathing liquid via a nostril of a face-down user maintains the liquid in prolonged and predictable contact with the nasal and sinus mucosa. A head orientation unit attaches to the head and includes an angle monitoring unit to provide an indication of the angular orientation of the head as it turns to optimize delivery of the liquid to target head structures. A liquid supply delivers the liquid through the user's nostrils to the selected head structures as a function of the angular orientation indication and at a pressure and flow rate that maintains a constant volume of liquid in the nasal and sinus cavities. Indicia on the angle monitoring unit permit the user to orient his/her head to predetermined angular positions.

15 Claims, 42 Drawing Sheets

(56) References Cited

U.S. PATENT DOCUMENTS

| | | | | |
|---|---|---|---|---|
| 5,474,564 A | * | 12/1995 | Clayman | A61B 90/11 128/898 |
| 5,738,517 A | * | 4/1998 | Keller | A61C 19/04 433/73 |
| 5,895,363 A | | 4/1999 | Preijde | |
| 5,899,878 A | | 5/1999 | Glassman | |
| 6,109,917 A | * | 8/2000 | Lee | A61C 19/045 433/68 |
| 6,228,070 B1 | | 5/2001 | Mezzoli | |
| 6,568,396 B1 | | 5/2003 | Anthony | |
| 6,609,523 B1 | | 8/2003 | Anthony | |
| 6,736,792 B1 | * | 5/2004 | Liu | A61H 35/04 222/211 |
| 6,758,218 B2 | | 7/2004 | Anthony | |
| 7,419,497 B2 | | 9/2008 | Muni et al. | |
| 7,771,409 B2 | | 8/2010 | Chang et al. | |
| 7,785,315 B1 | | 8/2010 | Muni et al. | |
| 7,835,784 B2 | * | 11/2010 | Mire | A61B 34/20 600/407 |
| 7,867,242 B2 | * | 1/2011 | Solar | A61B 90/11 606/130 |
| 7,925,328 B2 | * | 4/2011 | Urquhart | A61B 34/20 600/429 |
| 8,123,722 B2 | * | 2/2012 | Chang | A61B 34/20 600/101 |
| 8,414,473 B2 | | 4/2013 | Jenkins et al. | |
| 8,471,812 B2 | | 6/2013 | Bunch | |
| 8,690,839 B2 | * | 4/2014 | Xia | A61M 39/1011 604/187 |
| 2004/0045561 A1 | * | 3/2004 | Alexander | G09B 23/285 128/897 |
| 2004/0073178 A1 | | 4/2004 | Anderson et al. | |
| 2006/0156996 A1 | * | 7/2006 | Henry | A01K 1/0613 119/751 |
| 2007/0219600 A1 | * | 9/2007 | Gertner | A61N 5/0603 607/88 |
| 2008/0178871 A1 | * | 7/2008 | Genova | A61M 15/08 128/200.23 |
| 2009/0270796 A1 | | 10/2009 | Perry et al. | |
| 2009/0281485 A1 | | 11/2009 | Baker et al. | |
| 2010/0042046 A1 | | 2/2010 | Chang et al. | |
| 2010/0170508 A1 | * | 7/2010 | Genova | A61M 15/08 128/203.12 |
| 2011/0048414 A1 | * | 3/2011 | Hoekman | A61M 15/00 128/200.23 |
| 2011/0060214 A1 | | 3/2011 | Makower | |
| 2011/0087174 A1 | | 4/2011 | Carpenter | |
| 2011/0136073 A1 | * | 6/2011 | Basta | A61C 11/022 433/73 |
| 2011/0152838 A1 | * | 6/2011 | Xia | A61M 11/06 604/514 |
| 2012/0330239 A1 | | 12/2012 | Hoke et al. | |
| 2013/0158475 A1 | * | 6/2013 | Xia | A61M 39/1011 604/94.01 |
| 2015/0045775 A1 | * | 2/2015 | Xia | A61M 11/06 604/514 |

* cited by examiner

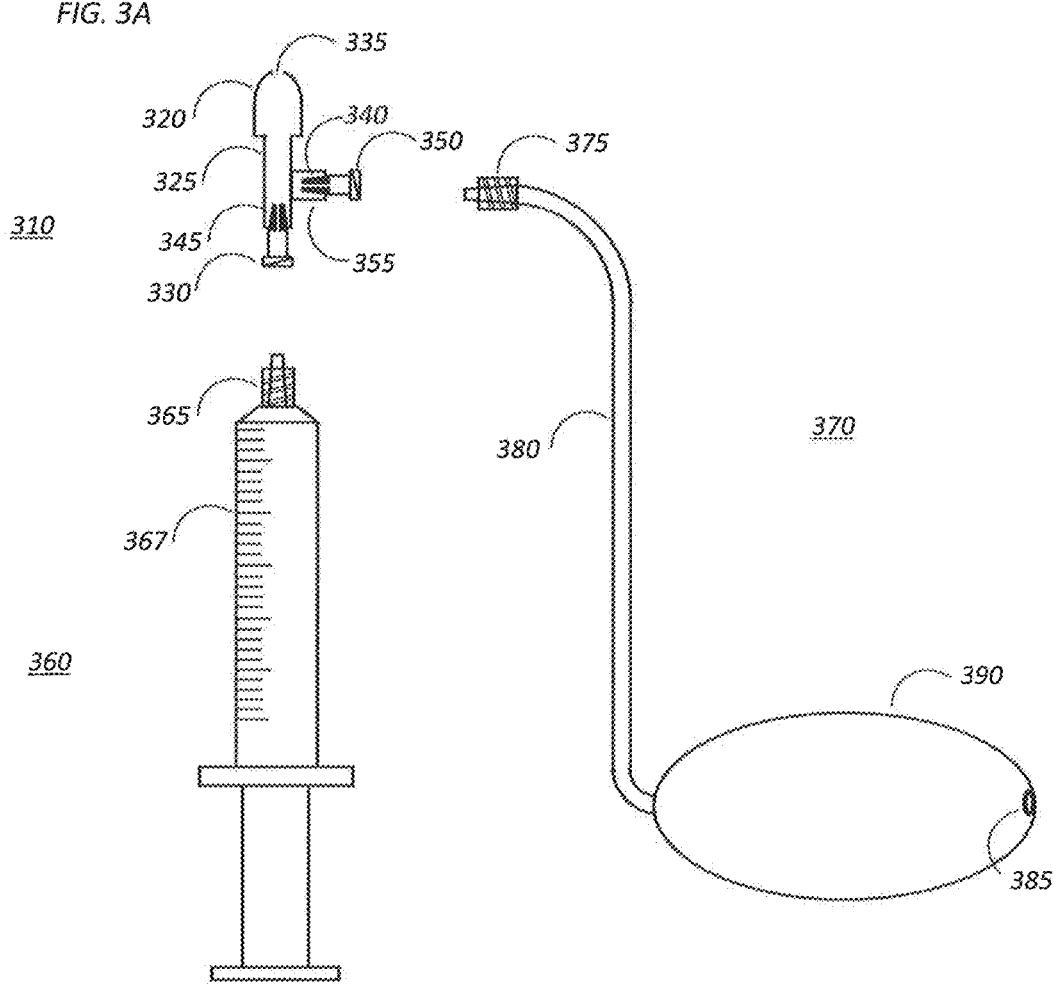

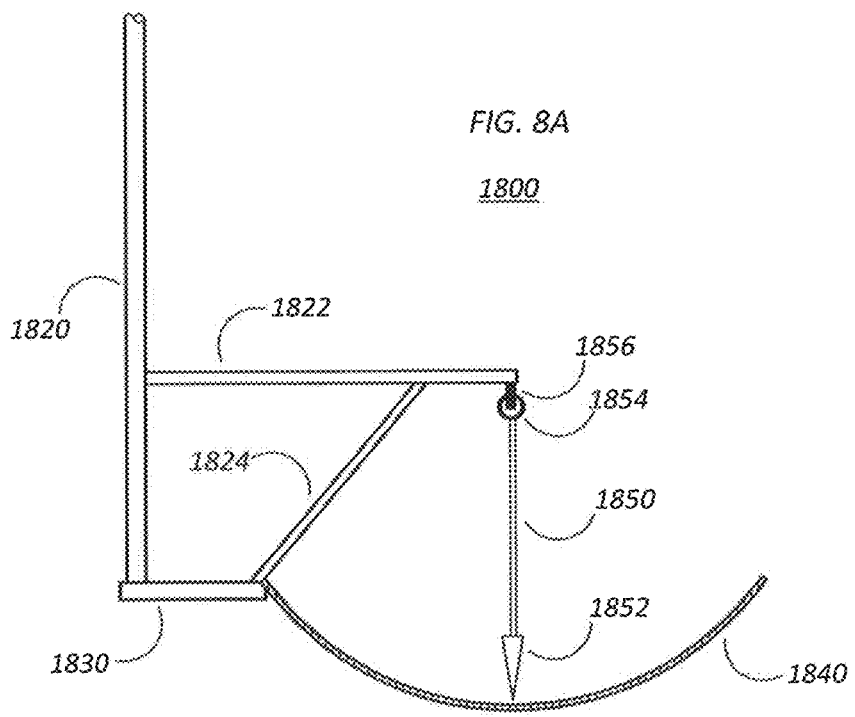
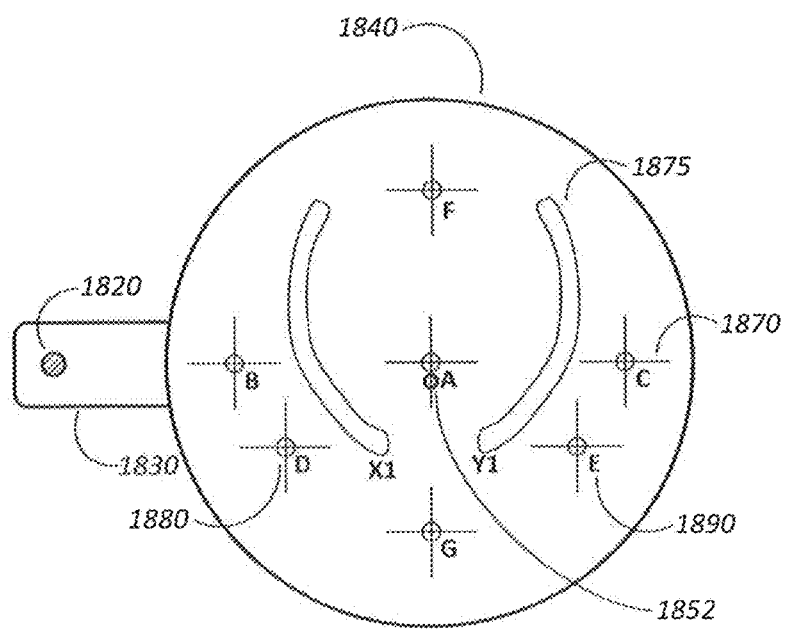

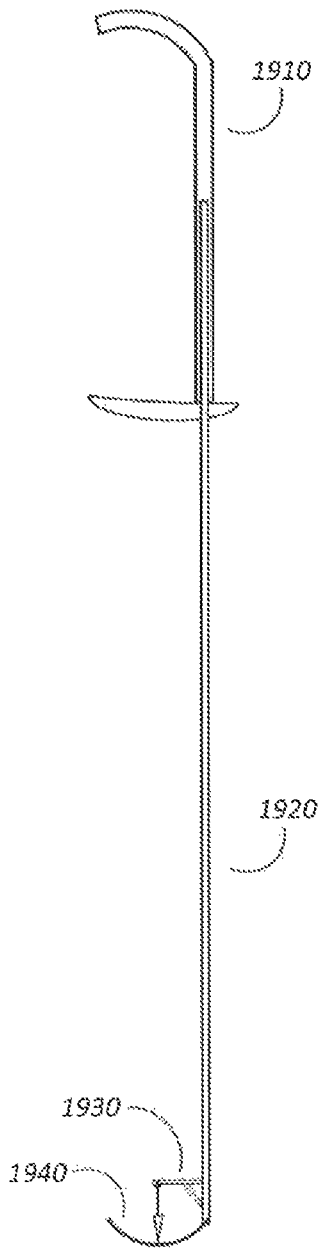

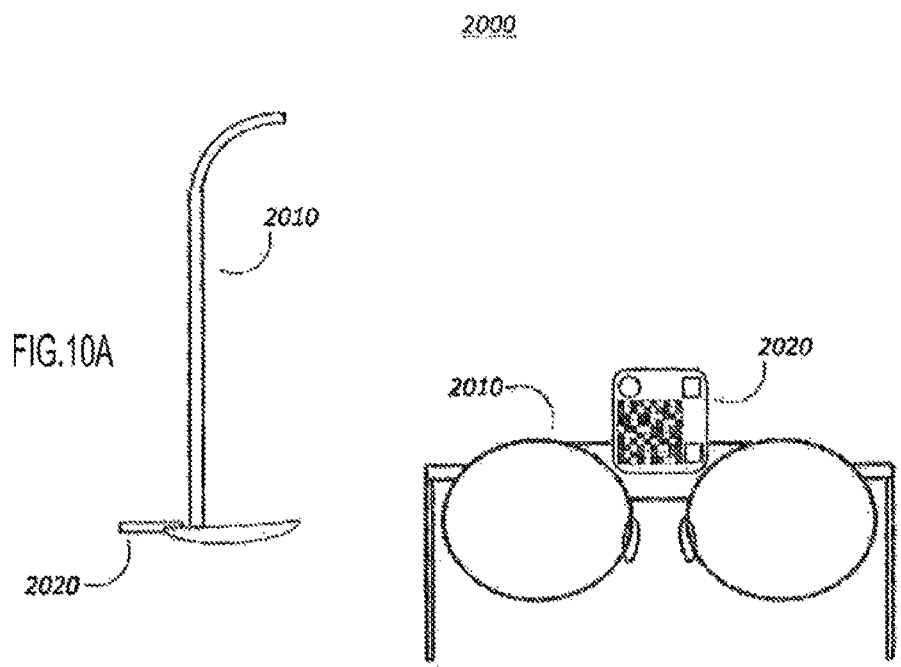
FIG.10A
FIG.10B
FIG.10C

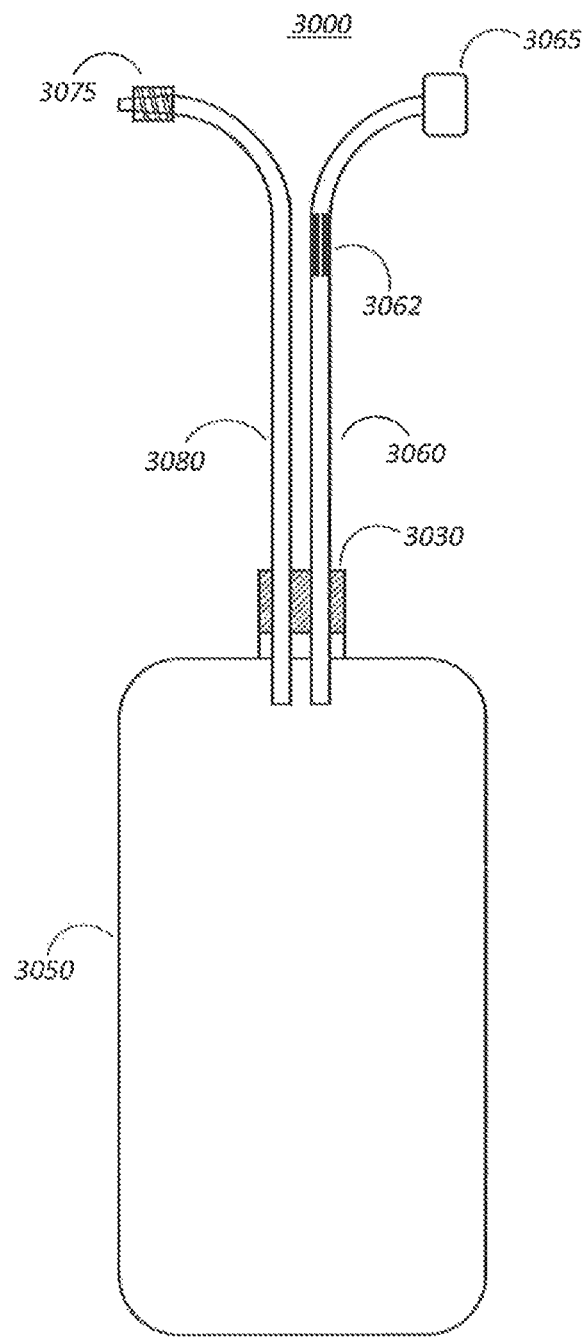

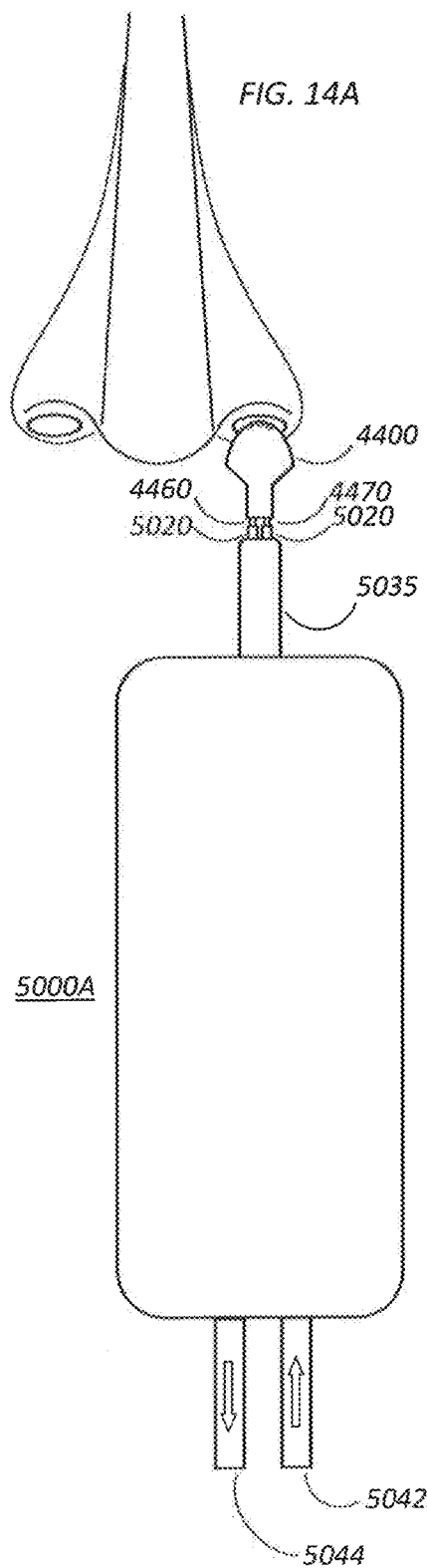
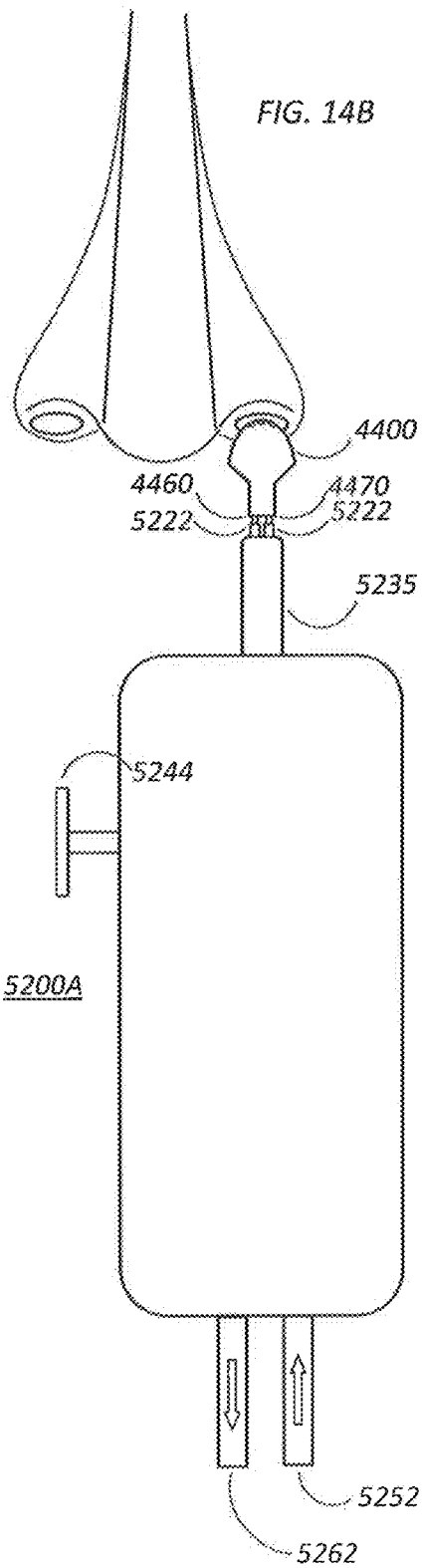

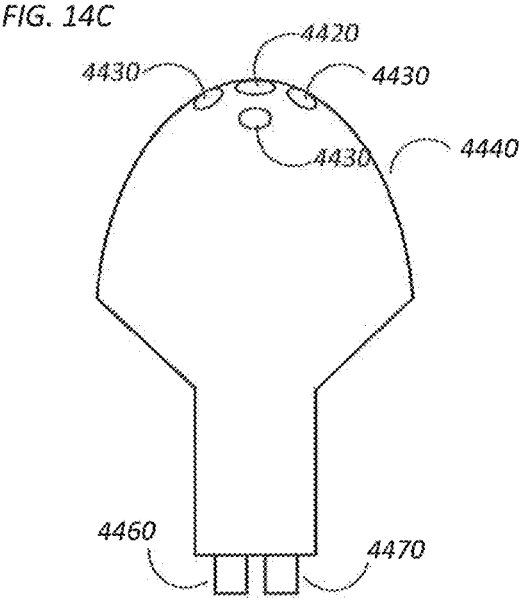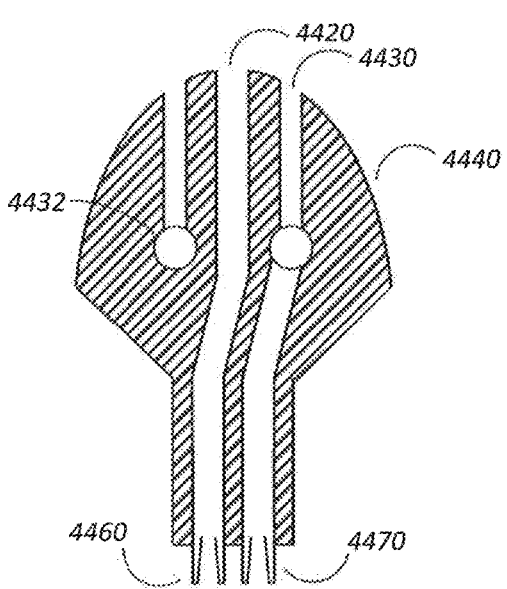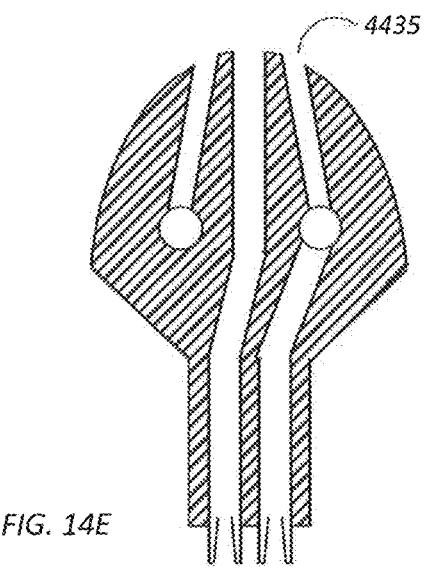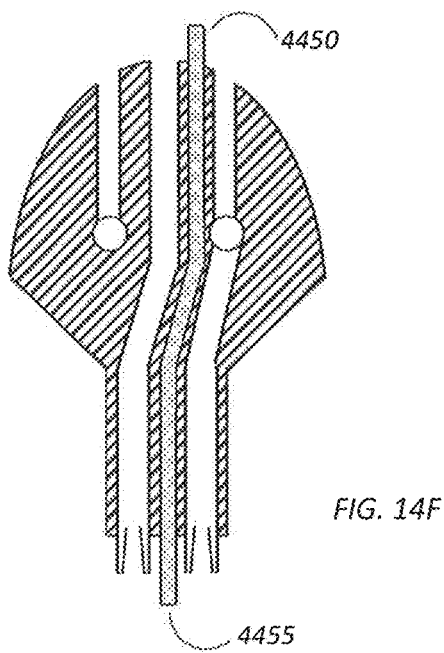
FIG. 14C
FIG. 14D
FIG. 14E
FIG. 14F

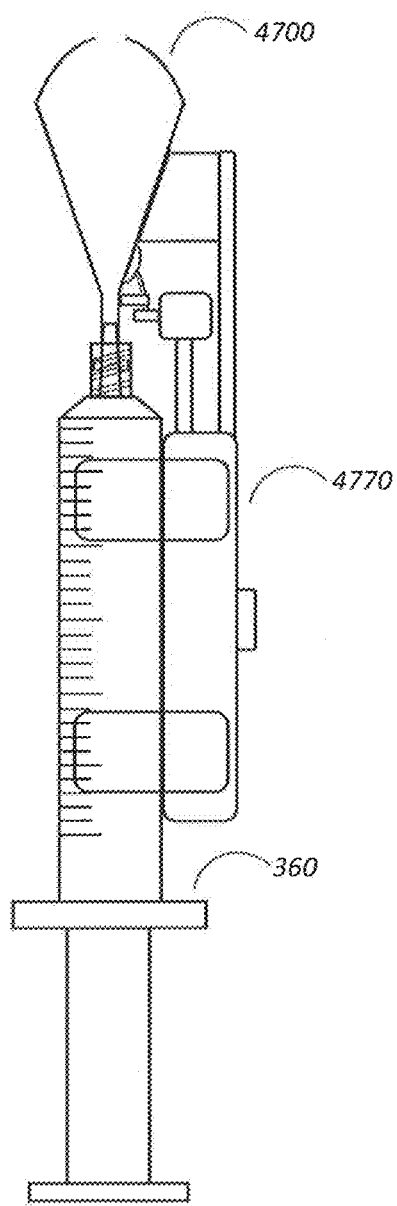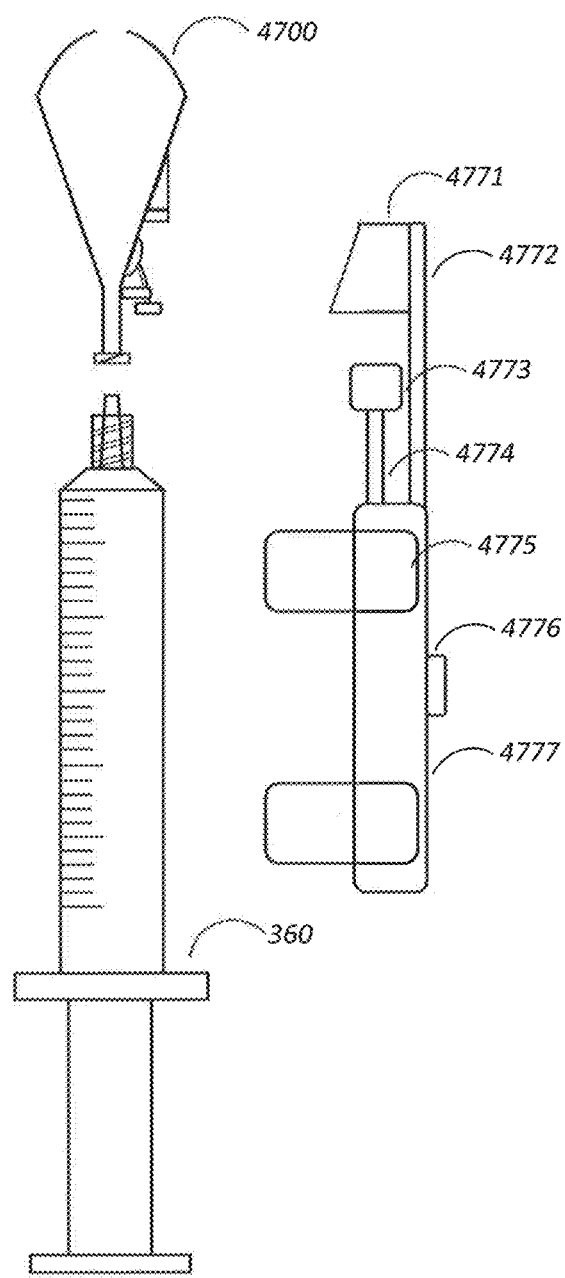

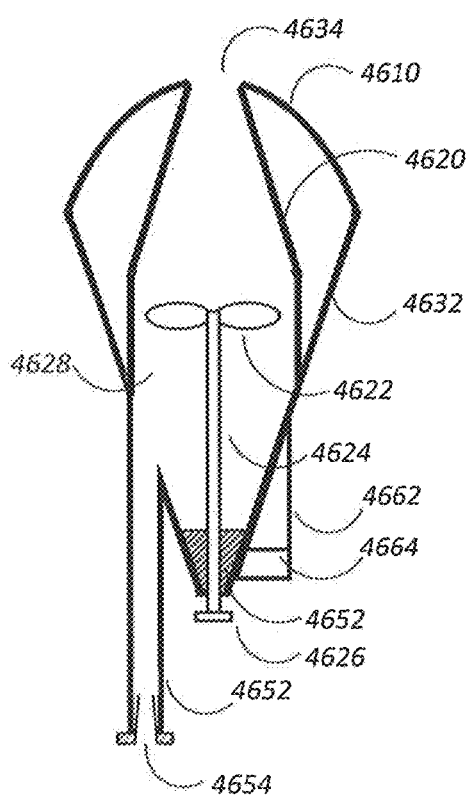
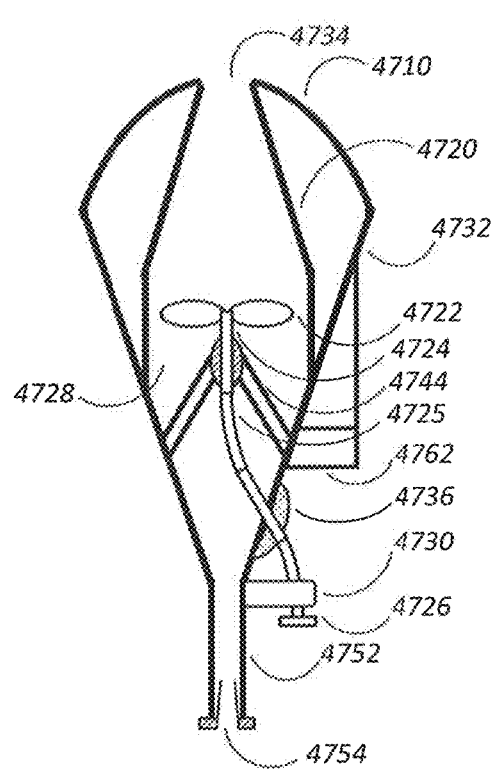
FIG. 16A
FIG. 16B

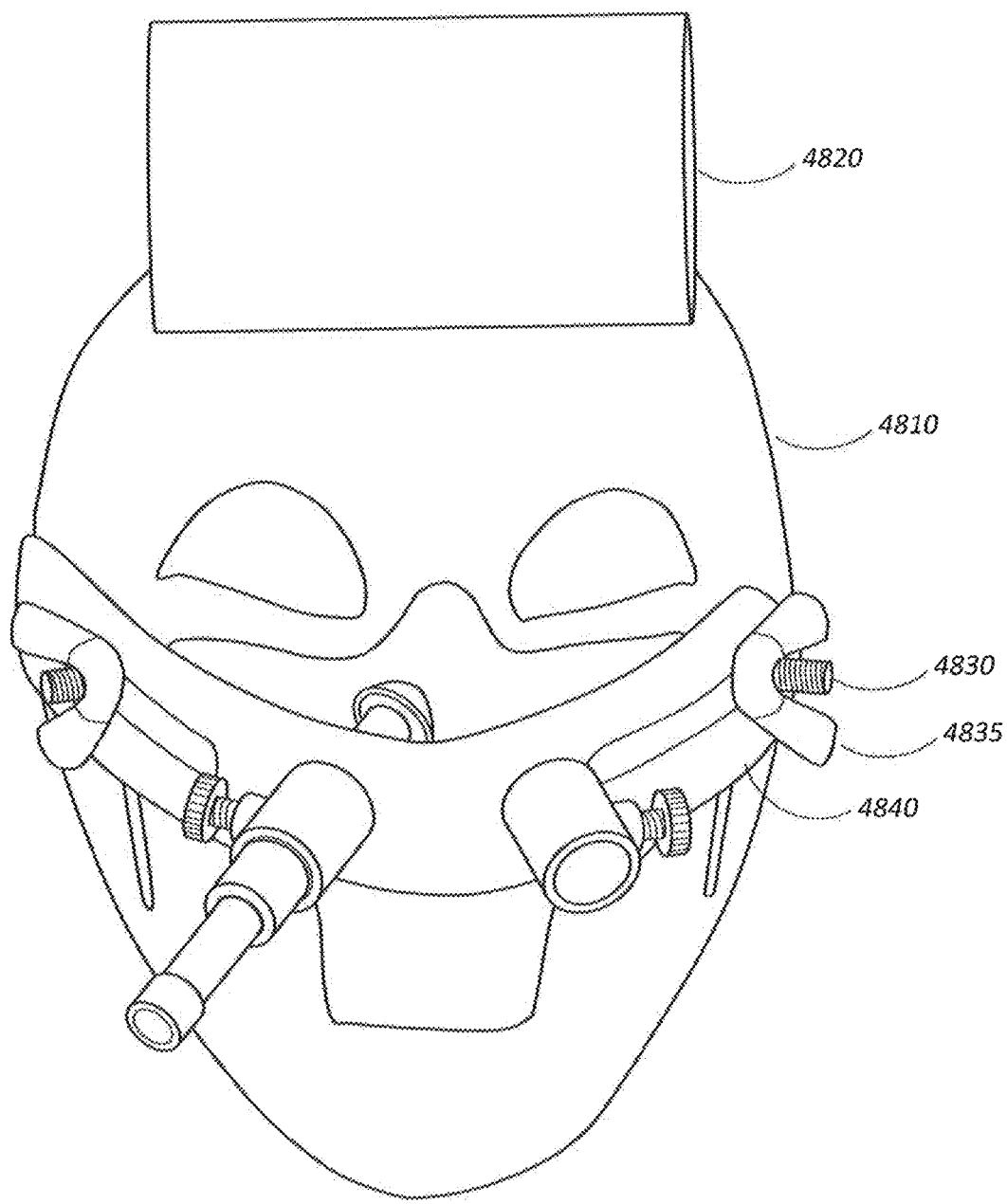

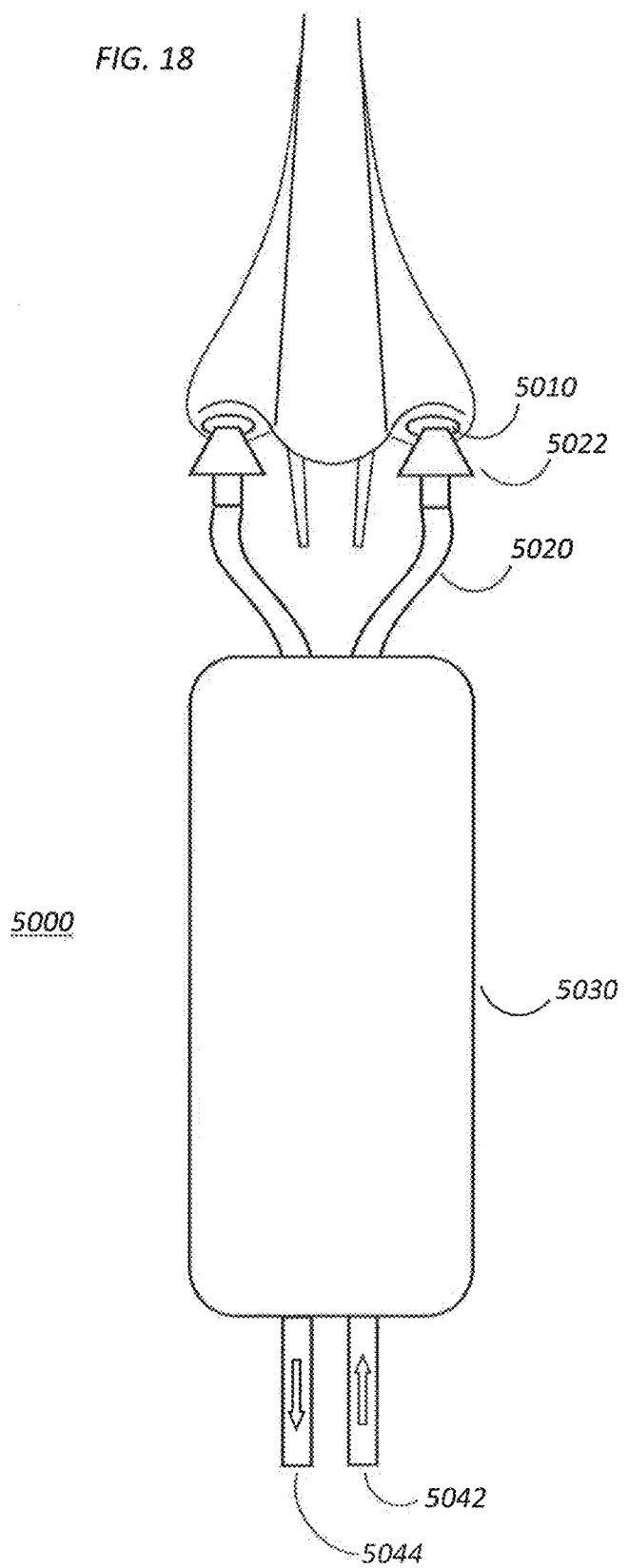

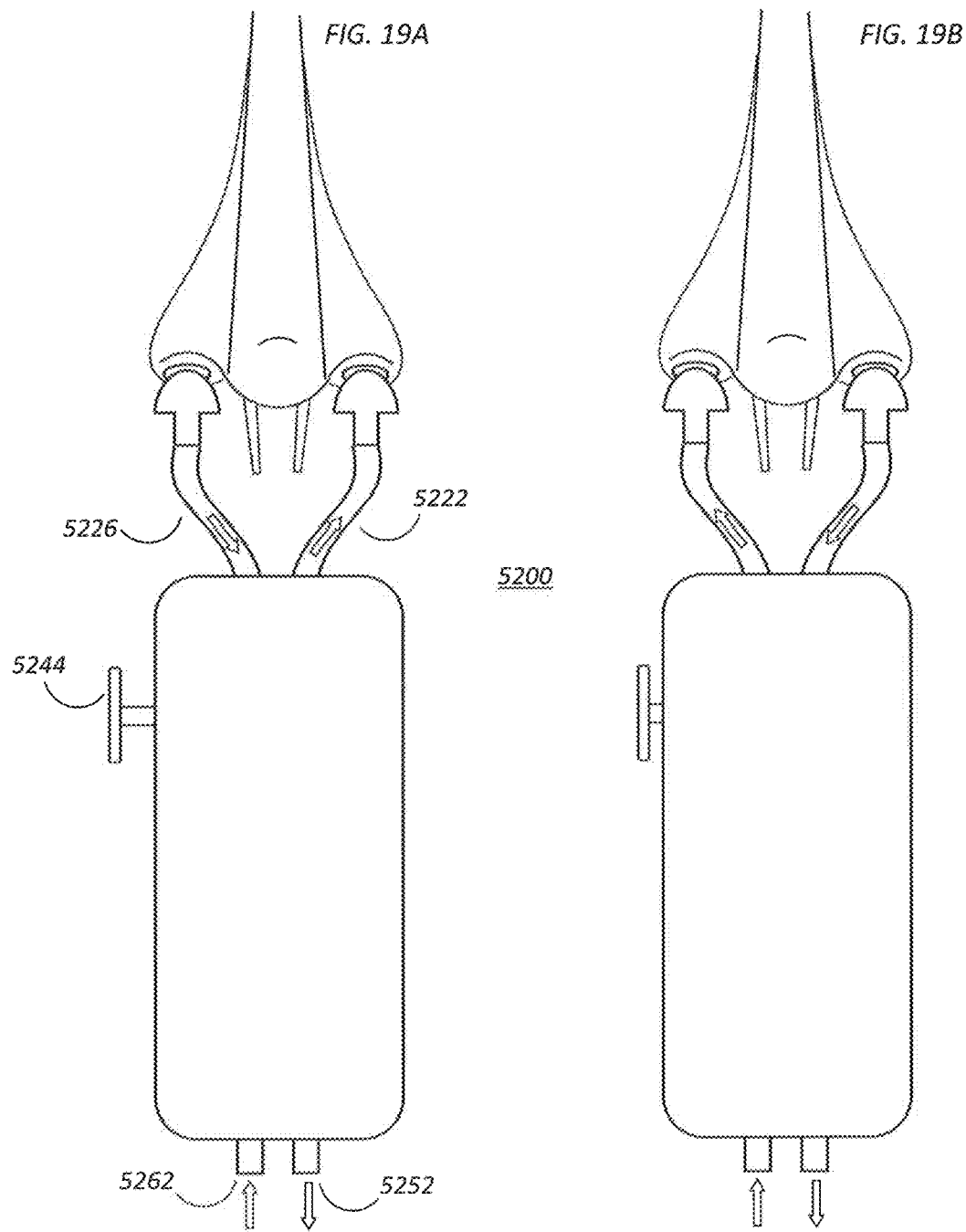

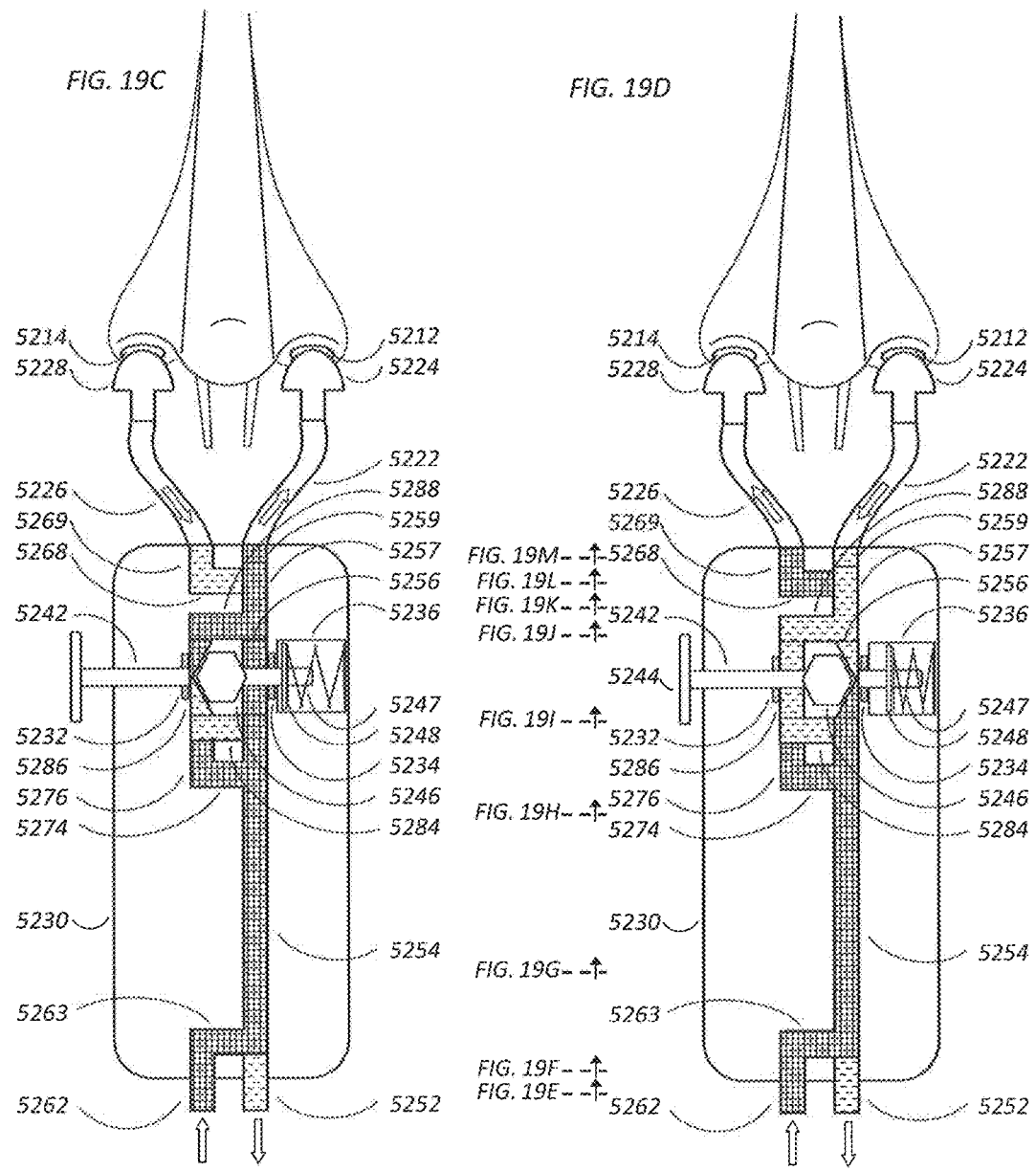

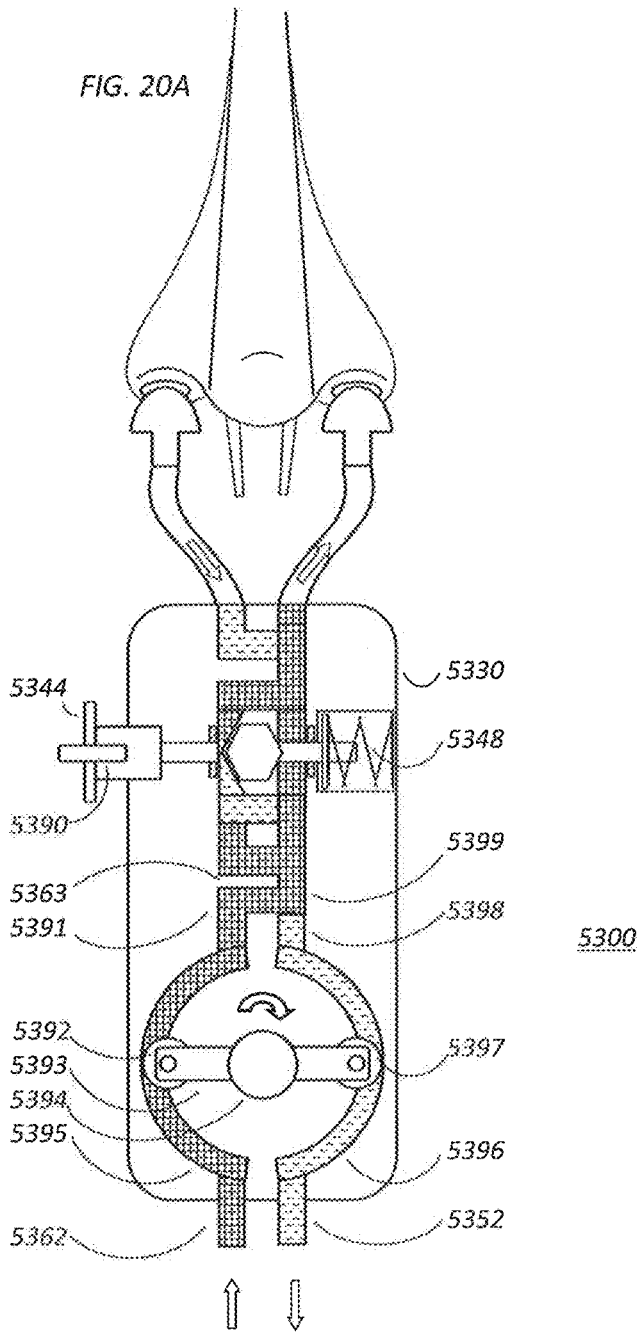
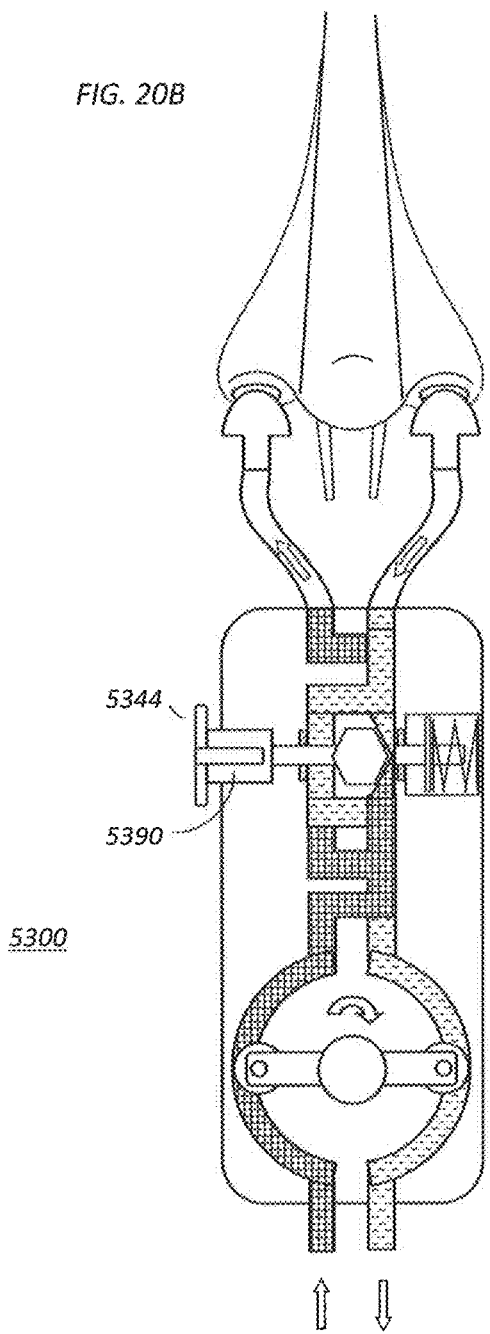
FIG. 20A
FIG. 20B

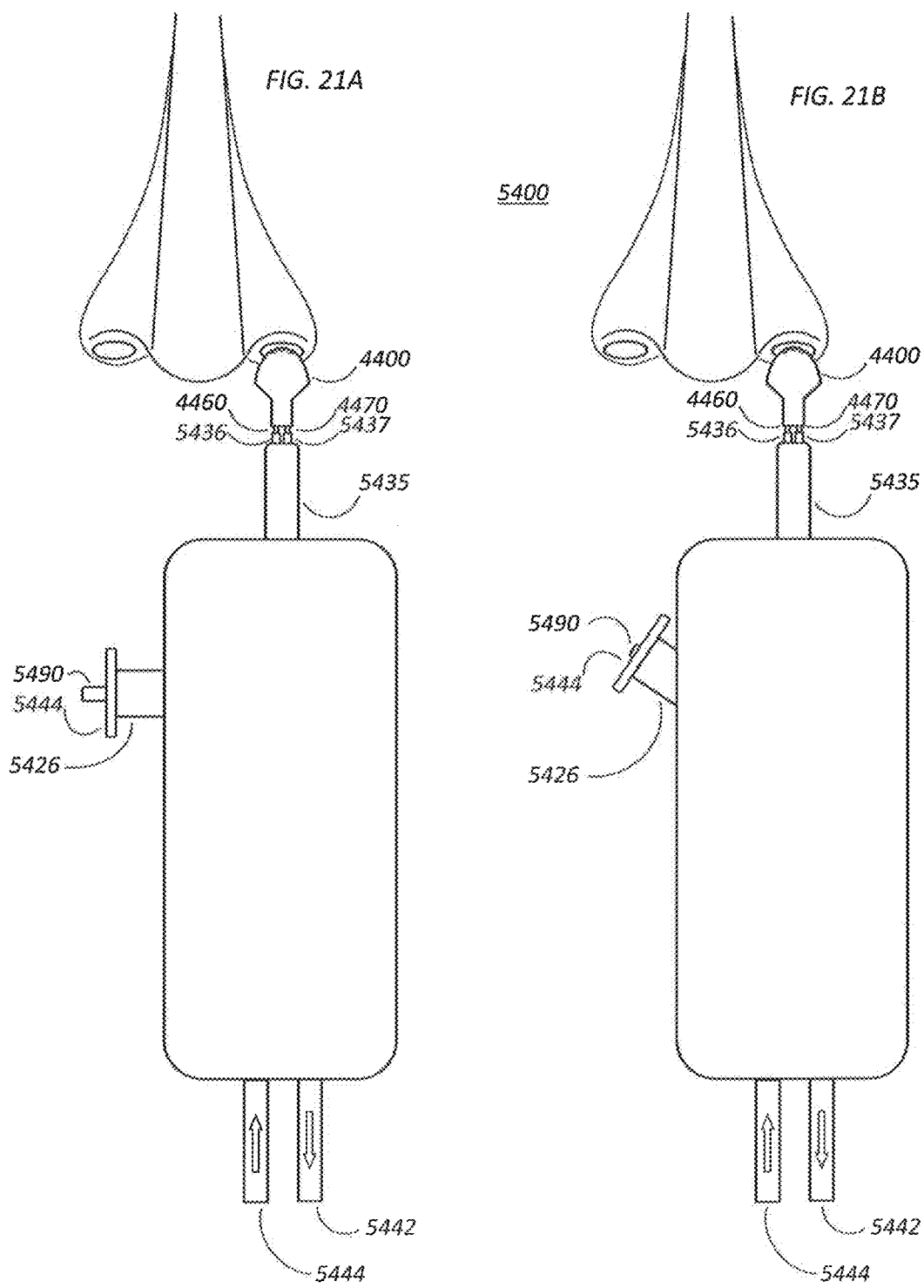

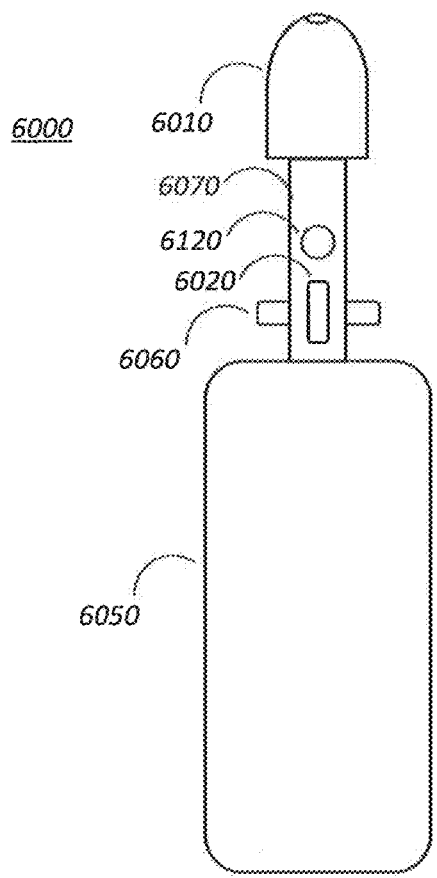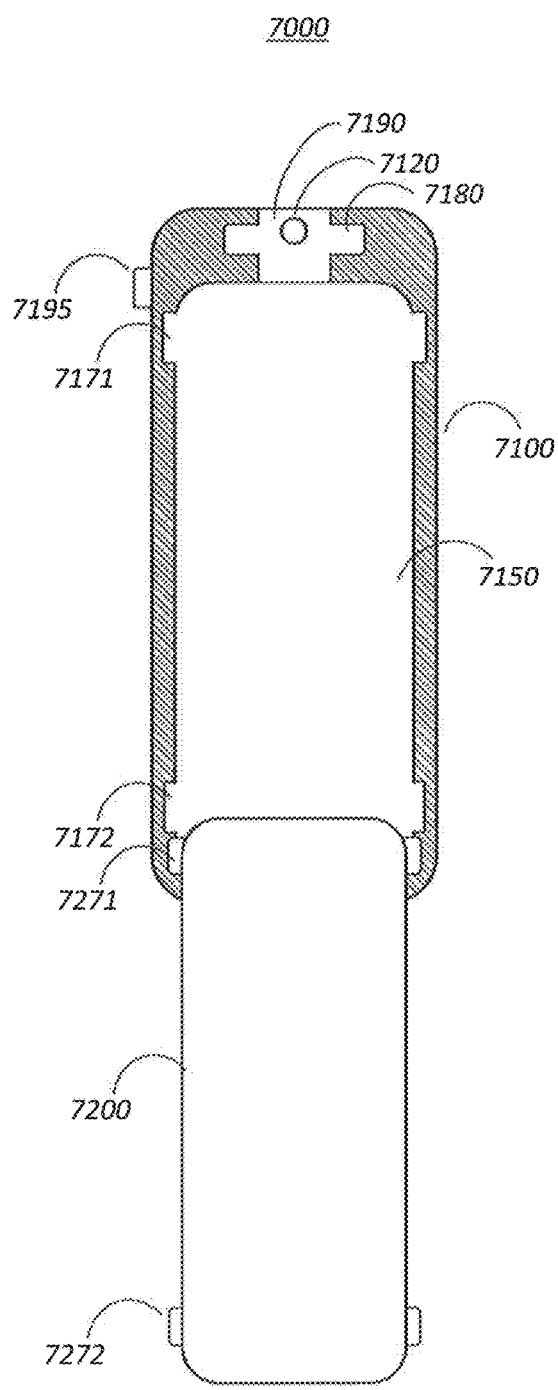
FIG. 22A
FIG. 22B

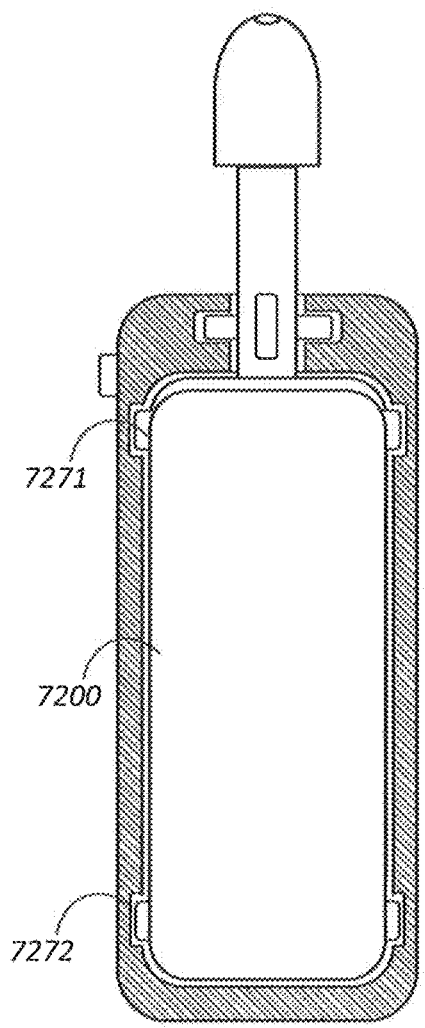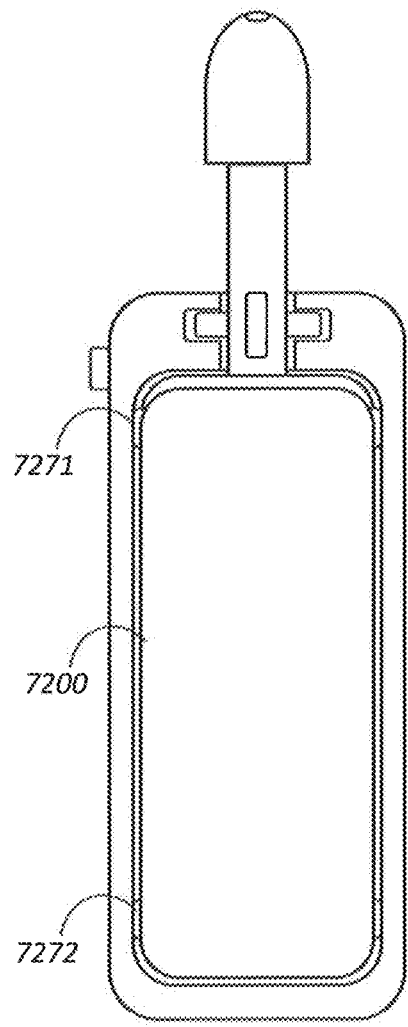
FIG. 22D
FIG. 22E

METHODS AND SYSTEMS FOR BATHING NOSE AND SINUS PASSAGES

CROSS REFERENCE TO RELATED APPLICATIONS

This application claims priority to U.S. Provisional Application No. 61/796,105, filed Nov. 2, 2012, by Michael Bart Siegel et al and entitled "Method And Apparatus For Bathing Nose And Sinuses", and to U.S. Provisional Application No. 61/852,192, filed Mar. 16, 2013, by Michael Bart Siegel et al and entitled "Method And Apparatus For Bathing Nose And Sinuses", the disclosures in which are incorporated herein in their entireties by this reference.

FIELD OF THE INVENTION

The present invention pertains to methods and systems for providing the nose, sinuses and other cavity and passage structures with prolonged exposure to a bathing fluid to clean and/or medicate those structures and/or to deliver drugs directly into the bloodstream and/or through the olfactory bulb/cleft to bypass the blood/brain barrier and first pass effect in the liver.

In addition, the invention pertains to angular displacement monitoring devices and methods for monitoring two dimensions of angular displacement from a vertical axis.

BACKGROUND

The human nasal cavity extends from the nares to the choana. Extending from this space, which is roughly rectangular, are four sets of sinuses which are hollow spaces in the bone of the head. The sinuses extend above, below, medial to and posterior to the boney orbit. The nasal and sinus cavities are normally able to clear mucous produced in their linings through a transport system called the mucociliary blanket, a self-cleaning lining of the nose and sinuses. The mucous is transported out of the sinus openings which vary from 1 mm in diameter to 2 cm in diameter and, in some cases, can be even larger. Normally, the mucous is then cleared out of the nasal cavity into the nasopharynx and down into the pharynx where it is swallowed. The mucocilliary blanket clears out viruses, bacteria, fungi and other debris from the nose and sinuses so that they do not have the ability to cause infection, both locally and systemically.

Sinusitis is caused by obstruction to the sinus ostia, or a breakdown of the mucocilliary clearance. The obstruction is caused by mucosal edema from viruses, allergies or any other irritants in inspired air. With the sinus ostia obstructed, mucous produced in the sinus accumulates and provides a perfect medium in which bacteria can grow. If an infection occurs, this leads to pressure in the sinus with facial pressure/pain, nasal obstruction, thick purulent nasal and post-nasal discharge and generalized fatigue.

Conventionally, patients are treated for sinusitis with oral antibiotics, steroid nasal sprays, decongestants and, occasionally, oral steroids. Nasal irrigations are used as well and are effective in clearing debris from the nasal cavity but are very irritating to the Eustachian tubes and pharynx. If the sinusitis does not clear after maximal medical therapy, or if the infections recur frequently, then surgery must be considered to enlarge the openings to the sinuses. Once the sinus openings have been enlarged, the sinuses are more accessible but are still poorly accessible with currently available nasal/sinus irrigation units. Sometimes the surgery is performed only with the idea that it will render sinus irrigations more effective. Even after such surgery, and despite the availability of many different devices, accessing the sinuses with saline or medicated liquid to clear the infection is still very ineffective.

In an article by Peter Wormald et al entitled "A Comparative Study of Three Methods of Nasal Irrigation" (*Laryngoscope*. 2004 December; 114(12):2224-7), the available methods of nasal and sinus irrigation are detailed and compared. The three techniques described are: nebulization (rhinoflow); nasal irrigation (metered nasal spray); and nasal irrigation in the Moffit's position (nasal douching with the top of the head positioned on the floor).

Nebulized medications are ineffective in entering the sinuses in any reliable fashion. Nasal rinse bottles are often effective in clearing the nose, but the irrigant rarely enters the sinus in any significant way. Even if the irrigant or nebulized saline enters the sinus, the contact time is very transient and unpredictable, thereby significantly minimizing its effectiveness. One reason for this is that the orientation of the user's head during fluid application is preferably face-down to permit the liquid to have access to all of the intended cavities. However, when the face down position is assumed in these prior techniques, the liquid tends to quickly flow out of the nasal passages without sufficient residence time to be effective and without contacting the target areas. To compensate for this some prior techniques for irrigation of the nose and sinuses introduce excess liquid into the nasal passage, often causing users to experience Eustachian tube irritation with subsequent ear pain and the discomfort of fluid draining into their throats, making them cough and choke.

Most conventionally used methods of delivering medication systemically through the nasal cavity are inaccurate and ineffective because of the transient and unpredictable contact time between the medication and the target membrane.

SUMMARY OF THE INVENTION

In one aspect, the present invention pertains to improving the effectiveness of bathing/irrigating and medicating nasal passages and sinus cavities by permitting selective increase in the residence time of the applied fluid in those head structures. Specifically, a primary use of the apparatus of the present invention is to provide prolonged and predictable contact with the nasal and sinus mucosa by a bathing fluid, and to deliver a saline bath or medication locally to the nose and sinuses to treat nasal/sinus conditions. The bathing fluid can be any fluid, preferably a liquid, that benefits the patient/user. This can include hypotonic, isotonic, and/or hypertonic saline and/or medications. The bathing fluid can be used to treat various nasal and sinus conditions including nasal/sinus infections and epistaxis.

The invention is also intended to provide prolonged and predictable contact to the nasal/sinus membranes, olfactory bulb and cleft by a bathing fluid to deliver medications systemically. The bathing fluid may include medications absorbed through the olfactory bulb, olfactory cleft or nasal and sinus mucosa. When medications are absorbed by the olfactory bulb, they bypass the liver, thereby protecting the medications from being altered by the liver. For this reason, and because medications absorbed through the olfactory bulb also bypass the blood/brain barrier, this invention provides an important medication delivery system.

To achieve the above and other results, the system of the present invention includes three primary components, namely, a Head Orientation Unit, a Fluid Introduction and Retention Unit and, optionally and preferably, a Fluid Agitation Unit, all of which individually and in concert comprise inventions disclosed herein.

The present invention allows the bathing liquid/fluid to bathe the nasal/sinus mucosa, olfactory cleft/bulb, by filling the nasal cavity and sinuses for various predefined periods of time.

In use, the Head Orientation Unit is first removably secured on the head of the patient/user, the unit being such that the unit orientation changes as the orientation of the head changes. The Head Orientation Unit may include any attachment member or device that can be temporarily affixed to the user's head, such as goggles with a strap or elastic band, a visor or cap, a helmet, etc. With the Head Orientation Unit in place and the user facing downward to look substantially at the floor, a head position indicator is suspended by a spacer bar from the attachment member below the user's face. The user then orients his/her head more precisely by tilting his/her head such that the head position indicator (e.g., a leveling bubble in one preferred embodiment) on a display unit is aligned with a mark or indicium that specifies the proper head orientation to bathe a particular target sinus or nasal structure. Different variations of this orientation of the head provide the optimal exposure to different sinuses or nasal structures, and each is associated with a respective indicium or mark. The Head Orientation Unit can also be used to define specific changes in the head orientation as may be useful, such as the Head Orientation Unit's ability to define a series or path of head orientations to cause the bathing fluid to enter certain specific areas of the nose and sinuses.

The Fluid Introduction and Retention Unit permits the user to "fill" the nasal cavity from the bottom, one or both sides at a time; in other words, the Fluid Introduction and Retention Unit establishes and supports a column of the bathing liquid in the nasal cavity to provide prolonged exposure to the liquid of structures in the cavity. Thus, the sinus cavities extending from the nasal cavity are reliably filled with bathing fluid, typically a saline or medicament liquid. In addition, filling one side of the nose until the smallest drop of bathing fluid is noted coming out of the opposite nares ensures no irritation to the user's Eustachian tube and that there is no discomfort of fluid draining into the throat. Keeping the head in this position allows the bathing fluid to remain in the sinuses indefinitely until the user releases the Fluid Introduction and Retention Unit from contact with the nostril, allowing the fluid to readily drain from the nose. Importantly, with this arrangement the liquid column in the nasal cavity is supported against gravity by the Fluid Introduction and Retention Unit in spite of the user facing directly downward.

The capacity of the syringe can vary depending upon how it is used; a 30 mL syringe is sufficient for many applications. The syringe is provided with gradation indicia to permit simple measurement of the amount of bathing fluid to be inserted. It is a simple matter to fill the Fluid Introduction and Retention Unit syringe by drawing the bathing fluid up through the syringe from its distal end.

The Fluid Agitation Unit can be used to introduce an agitation fluid, such as air, into the bathing liquid filling the nasal and sinus cavities. The agitation fluid creates turbulence in the liquid which assists in "scrubbing" the walls of the cavity structures to remove the thick sticky mucous and debris associated with inflammation and infection. Such aeration of the bathing fluid also assists in allowing the bathing fluid to fill the sinuses completely even in non-operated sinuses. It also creates a gentle massaging of the inside of the nose that soothes the tissue and simulates flushing the nose and sinuses without the discomfort of having saline flush into the Eustachian tubes and throat and mouth. Although aeration is one preferred form of creating the desired turbulence in the bathing liquid, other turbulence inducing means can be used as described hereinbelow.

In another aspect of the invention the bathing liquid is supplied in cartridges that can be pressurized (e.g., at the Fluid Introduction and Retention Unit) to deliver prescribed fluid volumes of bathing liquid. The complete or partial pre-filling of cartridges provides important benefits, such as convenience to the user as it eliminates the need to for the user to sterilize the bathing liquid. Another benefit of the cartridges is that the amount of fluid to be delivered is precisely controlled.

Another aspect of the present invention, independent of the sinus bathing application, is the provision of a novel general-purpose high-precision analog device for measuring angular deflection from vertical in two dimensions.

The above and still further features and advantages of the present invention will become apparent upon consideration of the following definitions, descriptions and figures of specific embodiments thereof wherein like reference numerals in the various drawing FIGS. are utilized to designate like components. While these descriptions go into specific details of the invention, it should be understood that variations may and do exist and would be apparent to those skilled in the art based on the descriptions herein.

BRIEF DESCRIPTION OF THE DRAWINGS

FIGS. 3A, 3B and 3C are partially diagrammatic views in elevation of the removable tip member and syringe, respectively, of FIGS. 2A and 2B wherein the tip member is modified and shown connecting with a Fluid Agitation Unit.

FIG. 8A is a partially diagrammatic view in elevation of another alternative Head Orientation Unit.

FIG. 8B is a partially diagrammatic top view in plan of the display of FIG. 8A.

FIG. 9 is a partially diagrammatic view in elevation of a Head Orientation Unit according to yet another embodiment of the present invention.

FIGS. 10A, 10B and 10C are diagrammatic illustrations of Head Orientation Units and a mobile device according to still further embodiments of the present invention.

FIG. 11 is a diagrammatic view of an alternative pump that can be used in place of the pump for the Fluid Agitation Unit of FIG. 3C.

FIGS. 14A, B, C, D, E and F diagrammatically illustrate alternative nozzles for Fluid Introduction and Retention Units according to the present invention.

FIGS. 15A and 15B diagrammatically illustrate additional alternative nozzles for Fluid Introduction and Retention Units according to the present invention.

FIGS. 16A and 16B diagrammatically illustrate still more alternative nozzles for Fluid Introduction and Retention Units according to the present invention FIGS. 17A through 17C diagrammatically illustrate an alternative hands-free Fluid Introduction and Retention Unit according to the invention.

FIG. 18 is a diagrammatic illustration of an alternative double-nozzle Fluid Introduction and Retention Unit according to the invention.

FIGS. 20A and 20B diagrammatically illustrate an alternative double-nozzle Fluid Introduction and Retention Unit with a built-in peristaltic pump.

FIGS. 21A through 21D diagrammatically illustrate a Fluid Introduction and Retention Unit with a means to selectively activate and deactivate the pumping of fluid out of the nasal cavity.

DETAILED DESCRIPTION

Figure 1:
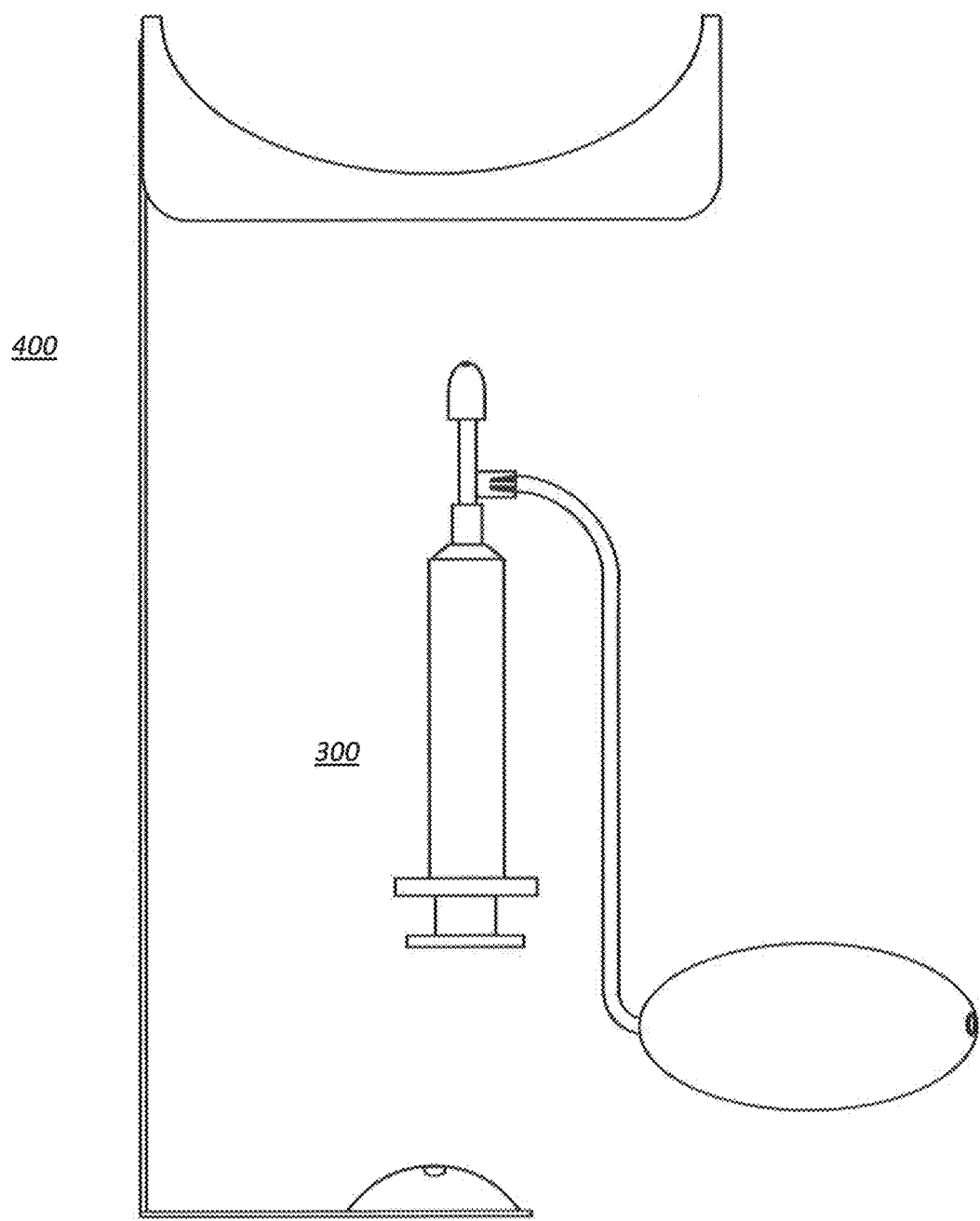
FIG. 1 is a partially diagrammatic view in elevation of a Fluid Introduction and Retention Unit and a Head Orientation Unit comprising one system embodiment of the present invention.

FIG. 1 illustrates a first system of the present invention comprising a Fluid Introduction and Retention Unit 300 and a Head Orientation Unit 400 according to one preferred embodiment of the present invention. The Fluid Introduction and Retention Unit 300 and Head Orientation Unit 400 are described in greater detail hereinbelow.

Figure 2A:
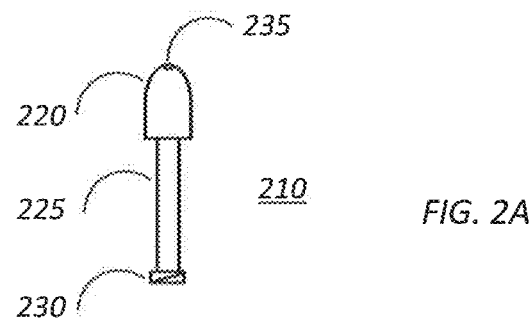
FIGS. 2A and 2B are partially diagrammatic views in elevation of a removable tip member and syringe, respectively, comprising the Fluid Introduction and Retention Unit of FIG. 1.
Figure 2B:
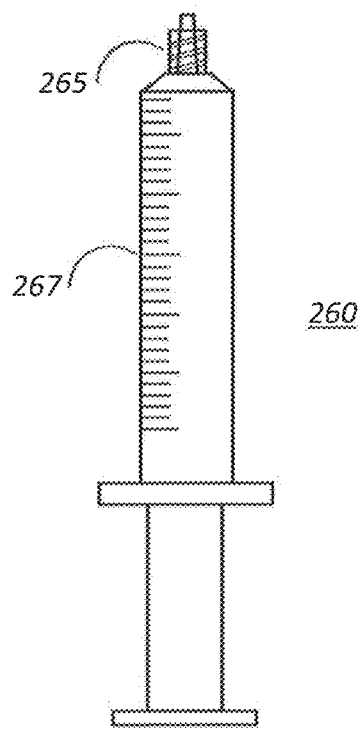

FIGS. 2A and 2B illustrate respective components of the Fluid Introduction and Retention Unit 300 of FIG. 1. Specifically, the Fluid Introduction and Retention Unit includes a removable tip member 210 and a syringe 260, the latter having a male Luer lock connector 265 at its distal end and a series of liquid measurement gradations 267 along its length. Removable tip 210 has a nostril interface 220 that forms a fluid-tight seal at the entrance to a patient's nostril. More particularly, nostril interface 220 has a generally cylindrical body with a hemispherical distal end and configured to project slightly into a user's nostril when the tip body forms the required fluid-tight seal. Tip 210 is affixed to tubular body 225 extending from its proximal end with a female Luer connector 230 that engages Luer lock 265 of the syringe. A channel or through bore 235 extends through the entire length of removable tip member 210 such that liquid from the syringe 260 can be transmitted therethrough and out from the distal end of the bore into the user's nostril.

FIGS. 3A through 3C illustrate a Fluid Introduction and Retention Unit 300 comprised of a removable tip member 310, a syringe 360 with a male Luer lock connector 365, and a Fluid Agitation Unit 370 adapted to connect and interact with the tip member according to another preferred embodiment of the present invention.

FIG. 3A is a cross-sectional view of removable tip member 310 which has a construction similar to tip member 210 (FIG. 2A) but is adapted to receive agitation fluid in the stream of bathing fluid that is issued from the tip member. Tip member 310 has a nostril interface 320 that forms a fluid-tight seal with a nostril when pressed against a nostril opening. Nostril interface 320 is affixed to tubular body 325 with a female Luer connector 330 at the proximal end of the tip member that engages male Luer connector 365 on the syringe. A channel or through bore 335 extends through the length of tip member 310 such that the bathing fluid from syringe 360 can be transmitted through the tip member and out through the distal end of nostril interface unit 320. An optional one-way valve 345 permits the introduction of clean fluids from syringe 360 into bore 335 through tip 310 while preventing the return of contaminated fluids back into syringe 360. An additive inlet port 340 is in fluid communication with bore 335 and extends generally laterally from body 325. Port 340 is provided with a female Luer lock connector 350 that selectively connects to a Fluid Agitation Unit 370 via tubing 380. An optional one-way valve 355 in inlet port 340 permits the introduction of clean fluid from Fluid Agitation Unit 370 into channel 335 while preventing the return of contaminated fluids back into Fluid Agitation Unit 370. Protecting syringe 360 and/or Fluid Agitation Unit 370 from contaminated fluids allows syringe 360 and/or Fluid Agitation Unit 370 to be reused without sterilization. In this arrangement, only removable tip member 310 needs to be disposable.

FIG. 3B illustrates syringe 360 and its male Luer lock 365 and gradations 367 demarking liquid content in the syringe.

FIG. 3C illustrates Fluid Agitation Unit 370 for introducing agitation fluids into the tip member 310. Male Luer lock connector 375 at the end of tubing 380 forms a fluid-tight seal with female Luer lock connector 350 of additive inlet port 340. The other end of tubing 380 is affixed to a hand pump 390, or the like. Squeezing hand pump 390 forces air, or other fluid, out of the hand pump through tubing 380 into channel 335 in tip member 310 and, from there, into the user's nostril. When the hand pressure is removed from hand pump 390, fresh air refills hand pump 390 through a one-way valve 385. It will be understood that other hand or motor actuated pumping apparatus may be used in place of a squeeze pump to deliver the pressurized agitation fluid into the bathing liquid stream in tip 310.

Figure 4A:
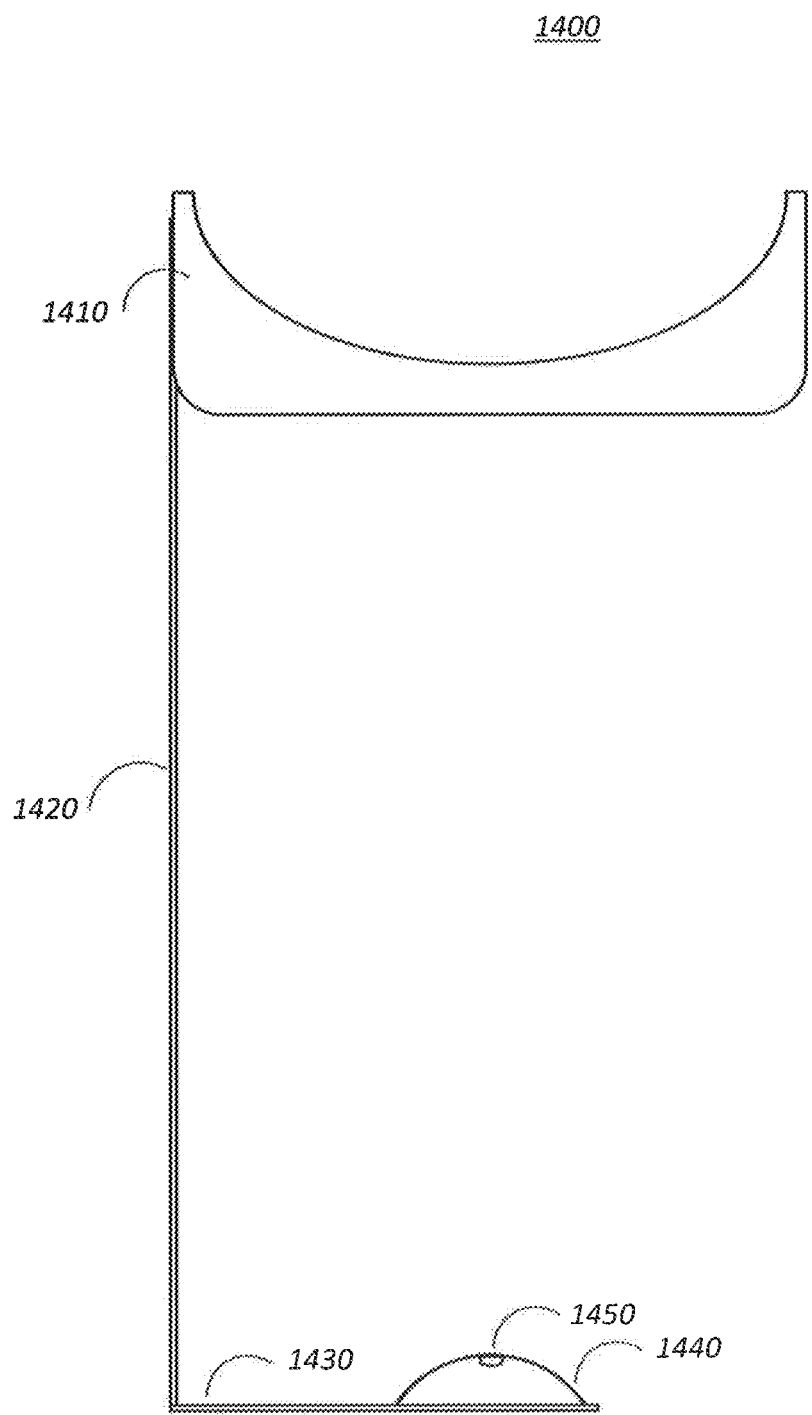
FIG. 4A is a partially diagrammatic view in elevation of the Head Orientation Unit of FIG. 1.
Figure 4B:
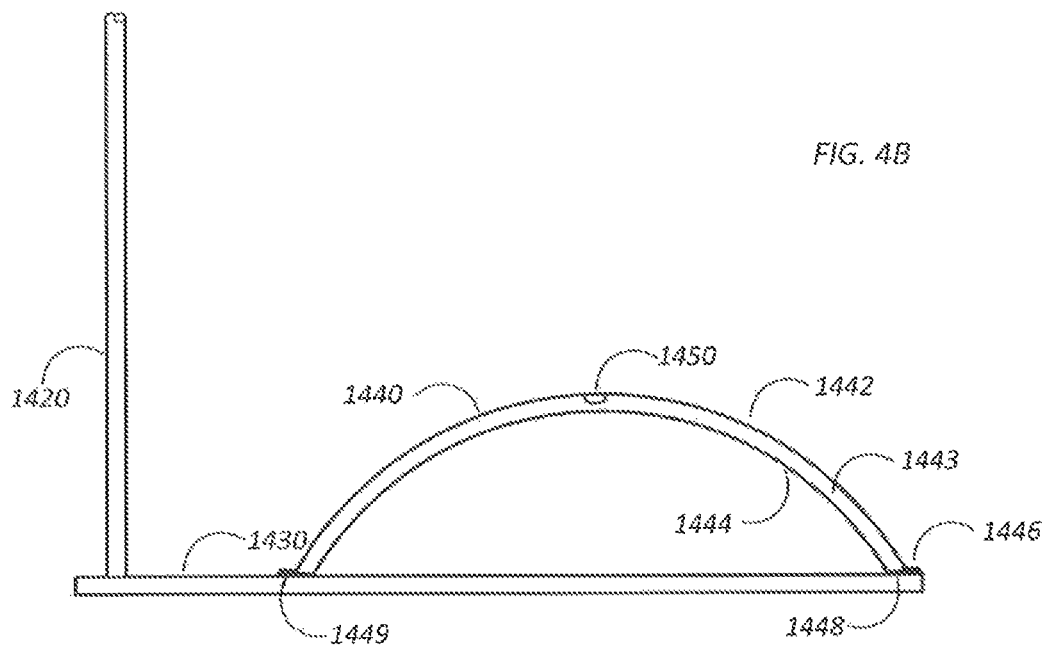
FIG. 4B is a partially diagrammatic view in elevation a head position display portion of the Head Orientation Unit of FIG. 1.
Figure 4C:
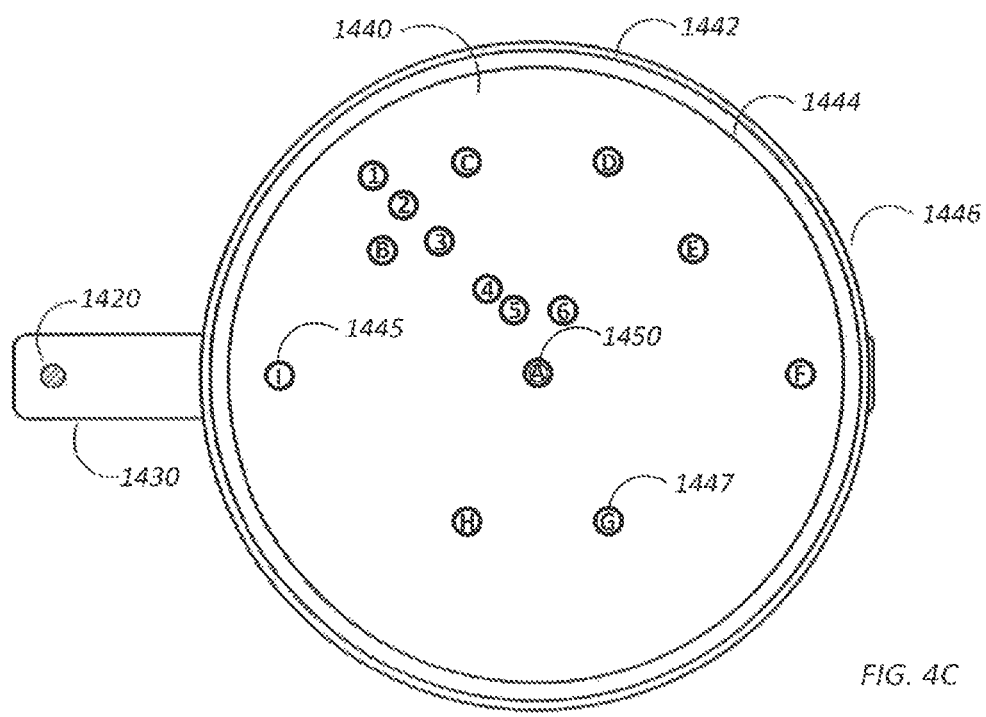
FIG. 4C is a top view in plan of the head position display of FIG. 4B.
Figure 4D:
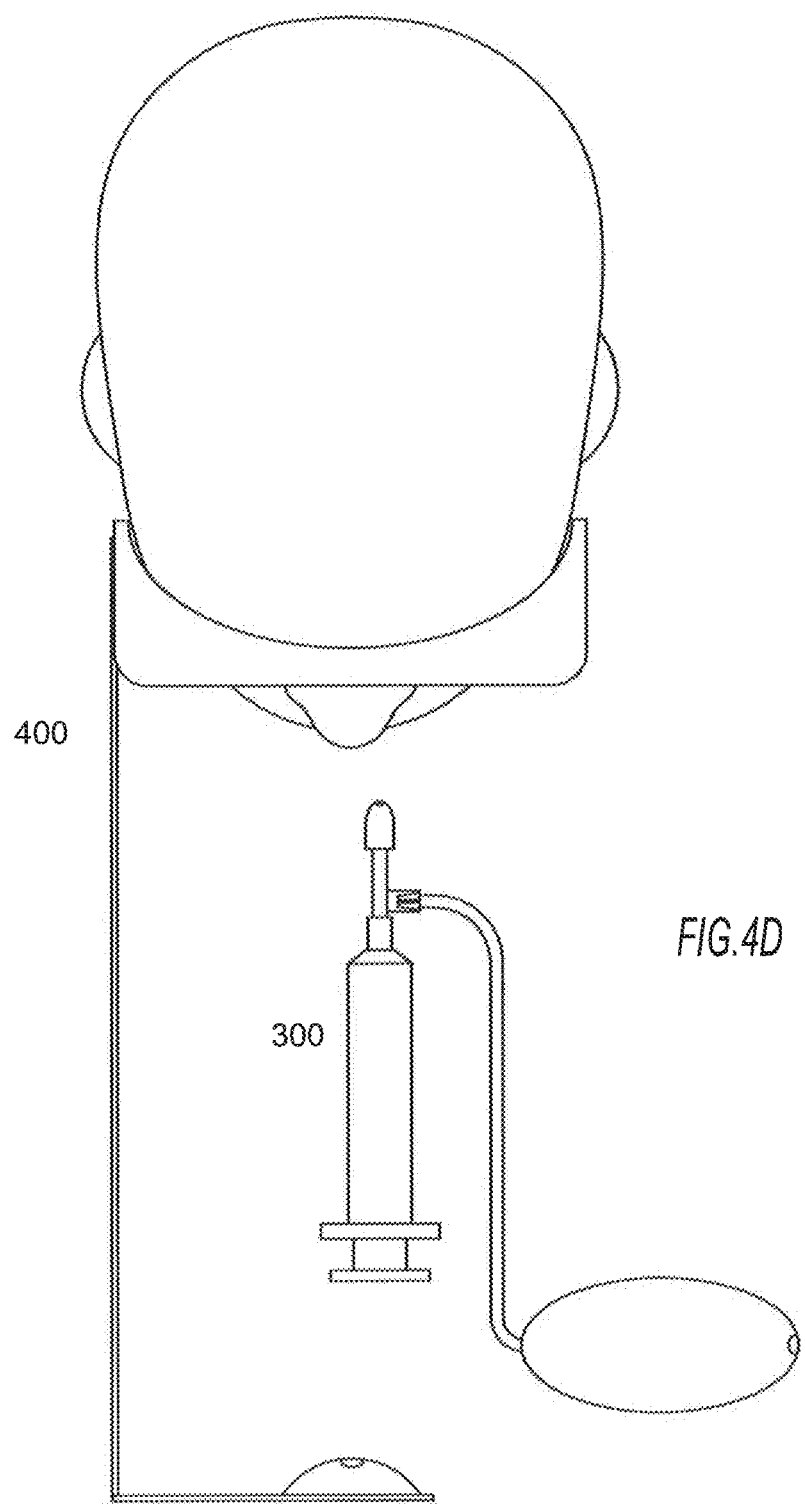
FIG. 4D is a partially diagrammatic view in elevation of the Head Orientation Unit of FIG. 4A disposed on the head of a patient/user.

FIGS. 4A through 4D illustrate Head Orientation Unit 1400 comprising an attachment member or head interface member 1410 shown secured to a user's head (FIG. 4D), a spacer arm 1420, display support arm 1430, and bubble level device 1440. Head interface member 1410, functioning as an attachment member to the user, can be a set of goggles held in place on the patient's/user's head by an elastomeric strap, a head band, a visor, or any other device that can be temporarily secured to and move with the patient's head. The proximal end of spacer arm 1420 is affixed to head interface member 1410 and the distal end is affixed to a display support arm 1430 extending substantially perpendicularly from the spacer arm. In this embodiment a bubble level device 1440 is affixed to the display support arm 1430 facing the head interface member so as to be visible to the user as shown in FIG. 4D. In this manner the display support arm 1430 is suspended from the head interface member 1410 at an angle to horizontal determined by the angular orientation of the user's head and the head interface member attached thereto. That angle is reflected by the position of a bubble 1450 in bubble level device 1440.

As illustrated in FIGS. 4B, 4C and 4D, bubble level device 1440 has a gas bubble 1450 in a liquid 1443 confined to a portion of a spherical shell. The shell is defined by a truncated spherical outer shell wall 1442 and a concentric truncated spherical inner shell wall 1444. This configuration maximizes the display area while minimizing the volume and weight of liquid 1443 in the bubble level device. Concentric spherical shell walls 1442 and 1444 can be vacuum formed from thin sheets of EVA, ethyl vinyl acetate, 0.020" in thickness. In one preferred embodiment the outer shell wall 1442 is thermoformed to an outer radius of curvature of 1.16", the spherical portion 2" in outer diameter; the inner shell wall 1444 is thermoformed to be parallel to and with a 0.1" distance between it and the outer shell wall 1442. The reveal 1446 of the outer shell wall 1442 is fused to a reveal 1449 of the inner shell wall 1444, for example, by ultrasonic welding. The reveal 1449 of the inner shell wall 1444 is fused to the acrylic display support arm 1430.

In fabricating the level device, a tapered hollow needle can pierce the reveal 1449 of the inner shell wall 1442. The needle can then be withdrawn slightly, the tip still inside the shell. The result is a hole or aperture 1448 extending through inner shell wall 1442. The slight withdrawal of the needle leaves an air gap between outside of the needle and aperture 1448. The gap permits air to escape the shell while it is being filled with liquid 1443. The liquid 1443 is injected through the hollow needle into the shell. Enough liquid 1443 is introduced into aperture 1448 to fill the shell, except for the small amount that will produce bubble 1450. After the shell is sufficiently filled, the hollow needle is withdrawn and aperture 1448 can be sealed by adhesive tape, or the like. The shell is protected from damage caused by potential freezing of the liquid 1443 by using, for example, a concentrated saline solution as the liquid 1443. The liquid 1443 can be colored by the addition of a colorant such as hydrophilic ultramarine pigment.

Outer shell 1442 has indicia 1447 printed or otherwise defined thereon at locations. The indicia can be, for example, circles whose diameter is about the same as the diameter of the air bubble 1450. The alignment of bubble 1450 to each indicium of indicia 1447 corresponds to a predetermined head orientation that is optimal for the introduction and retention of fluid to, or into, one or more nasal, sinus or other head structures. Each indicium of indicia 1447 has a label 1445 designating the head structure(s) for which its orientation is optimized. Each indicium of indicia 1447 and its label 1445 can be a color, such as fluorescent orange, designed to enhance its visibility. Thus, a user can selectably optimize the introduction and retention of fluid to, or into, particular nasal, sinus or other head structure(s) by orienting (titling) his/her head such that bubble 1450 is aligned with an indicium of indicia 1447 designating the particular nasal, sinus or other head structure(s).

Numerals "1" through "6" provided in respective indicia 1447 illustrate how a path of successive head orientations can be defined on the display for a particular irrigation or other treatment. For example, the user first adjusts his/her head to the orientation marked "1", then to the orientation marked "2", and so on, in sequence.

The display is shown as having a circular periphery; however, this shape can be different depending upon the optimal variations in useful display angles for various treatment modalities.

Other shapes can be used for such large display, lightweight bubble level devices. For example, the display can be all or a part of a toroidal shell. Here the radius of curvature in one-dimension is much less than the radius of curvature in the perpendicular direction.

The radius of curvature at a particular orientation can be varied such that it is smaller where the preferred resolution is less, and larger where the preferred resolution is greater. For example, a shell bounded, at least in part, by parallel ellipsoids of revolution will have a greater resolution the closer the major axes of the ellipsoids are to horizontal. The curvature of the shell walls can be any of many curves, such as the sums of trigonometric, polynomial and/or other functions and/or combinations thereof. To minimize the weight and volume of the fluid while optimizing the display area, the shell at a particular orientation of the level should have a thickness slightly greater than the depth of the bubble for each useful orientation of the level device.

In addition to its use in the present invention to display head orientation, the thin shell bubble head orientation unit is a novel general-purpose high-precision analog device for measuring angular deflection from vertical in two dimensions. As used in the head orientation display described herein, the two dimensions are roll (rotation about the axis extending longitudinally through the spine) and yaw (rotation perpendicular to that axis).

The descriptions immediately below and FIGS. 5A through 5D, 6A through 6F, 7A and 7B, 8A through 8C, 9, and 10A and 10B pertain to the details of alternative Head Orientation Units.

Figure 5A:
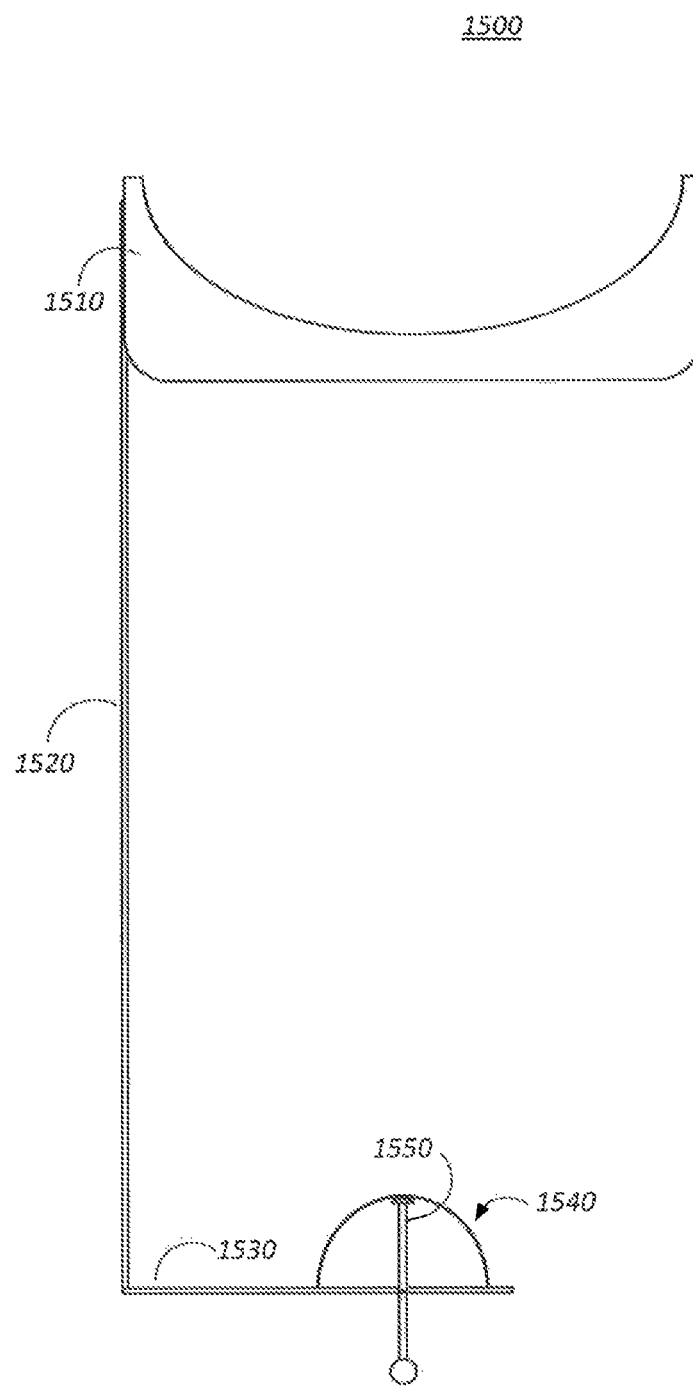
FIG. 5A is a partially diagrammatic view in elevation of Head Orientation Unit according to another embodiment of the present invention.
Figure 5B:
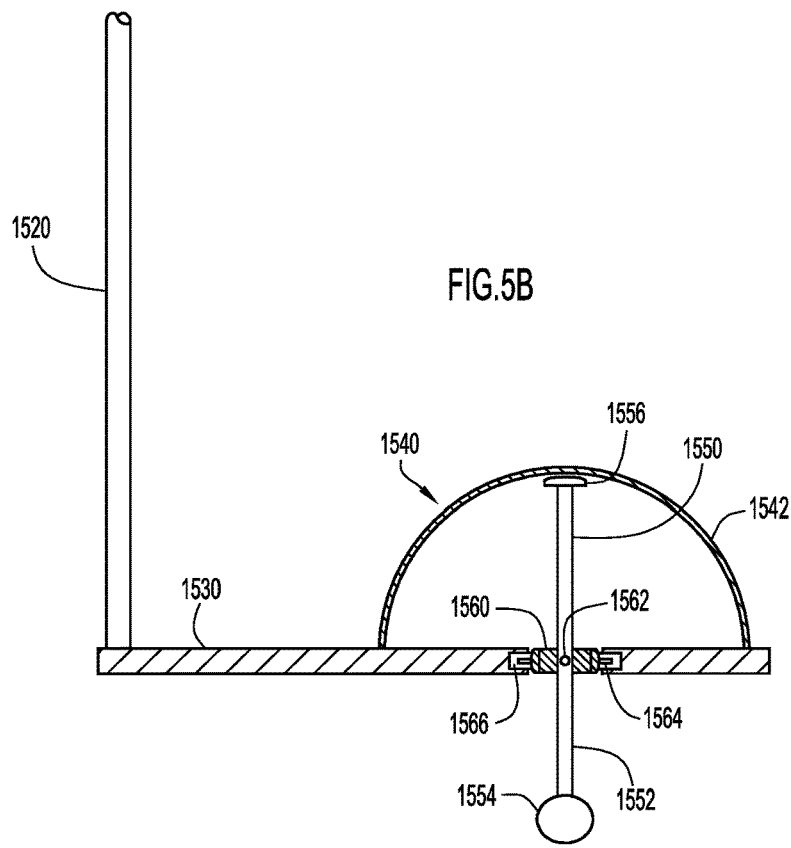
FIG. 5B is a partially diagrammatic view in elevation a head position display portion of the Head Orientation Unit of FIG. 5A.
Figure 5C:
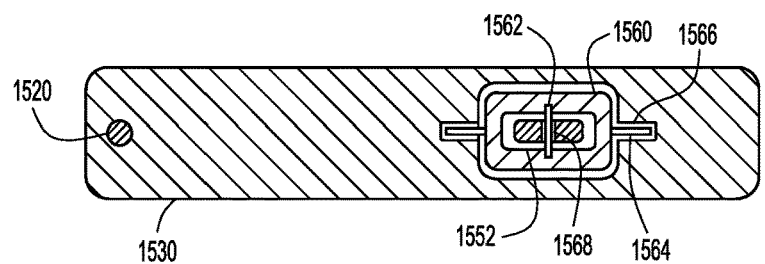
FIG. 5C is a top view in section of a portion of the display of FIG. 5B.

FIGS. 5A through 5D illustrate an alternative Head Orientation Unit 1500 comprising a head interface member 1510, a spacer arm 1520, a display support arm 1530, and a gimbal-mounted vertical pointer/display unit 1540. The head interface or attachment member 1510 can be any device, such as a set of goggles, held in place on the patient's head by an elastomeric strap, or the like. One end of spacer arm 1520 is affixed to head interface member 1510 and the other end is affixed to display support arm 1530. Vertical pointer/display unit 1540 is affixed to display support arm 1530. Vertical pointer/display unit 1540 comprises a display 1542, double-gimbal mount 1560 and a vertical pointer 1550. Display 1542 can be a transparent spherical shell thermoformed in plastic. Display 1542 has indicia 1557 similar to indicia 1447, for example, circles, at one or more locations. Each indicium 1557 has a label, similar to labels 1445, designating the head structure(s) for which its orientation is optimized. Each indicium 1557 and its label can be a color, such as fluorescent orange, designed to enhance its visibility. Display 1542 is shown as having a hemispherical outer shape. This shape can be different depending upon the optimal variations in useful display angles for various treatment modalities. FIGS. 5B and 5C illustrate double-gimbal mount 1560 and vertical pointer 1550. Double-gimbal mount 1560 can be a single piece of molded plastic and comprises the main body with outer axle 1564 and inner axle 1562. Each part of outer axle 1564 freely turns in its own cylindrical hole 1566 in display support arm 1530. Inner axle 1562 freely turns in aperture 1568 in vertical pointer shaft 1552. Vertical pointer 1550 comprises vertical pointer shaft 1552, vertical pointer weight 1554 and vertical pointer head 1556. Vertical pointer weight 1554 makes the bottom of the vertical pointer heavy enough to assure that the vertical pointer shaft 1552 will always be parallel to the vertical direction when the unit is in use. The double-gimbal mount allows the vertical pointer 1550 to have a vertical orientation independent of the orientation of display support arm 1530. As illustrated in FIG. 5B, vertical pointer head 1556 is close to the inside of display 1542 and can be seen through display 1542.

Figure 5D:
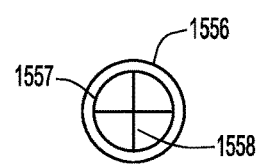
FIG. 5D is a top view in plan of a pointer head used in the display if FIG. 5C

FIG. 5D illustrates details of the vertical pointer head. Vertical pointer head 1556 can have a cross-hair indicium 1558 that the user can use to accurately align his/her head orientation with the specified indicium 1557 on the surface of display 1542. Indicia 1557 and 1558 can be brightly colored to enhance their visibility.

FIGS. 6A through 6F relate in detail to an alternative Head Orientation Unit 1600 comprising a head interface member 1610 like units 1510 or 1910 (described below in relation to FIG. 9), a spacer arm 1620, display support arm 1630, and a display platform 1640 supporting an array of bubble level devices 1660. Each bubble level 1660 can be affixed to display platform 1640 by a bubble level support rod 1650. Each bubble level support rod 1650 permits each bubble level 1660 to be oriented at a specified angle with respect to the plane of the display platform 1640. Thus, the bubble 1685 in a given bubble level 1660 can be centered in the level cross-hairs 1670 and/or level center target 1680 only when its bubble level 1660 is horizontal, corresponding to a predefined orientation of the Head Orientation Unit 1600 with respect to horizontal. This correlates to a pre-defined orientation of the user's head to the vertical. Each bubble level 1660 can bear an indicium 1690 to identify that specific bubble level 1660 and its corresponding orientation with respect to the horizontal plane. By moving his head such that the bubble 1685 of a bubble level 1660 specified by indicium 1690 is centered on that bubble level 1660, the user can precisely orient his head to optimize the filling of a given sinus with bathing fluid. By moving his head to follow a specified path of bubble levels 1660, the user can perform complex movements to optimize the exposure of structures in or near the nasal cavity to useful liquids.

Figure 6A:
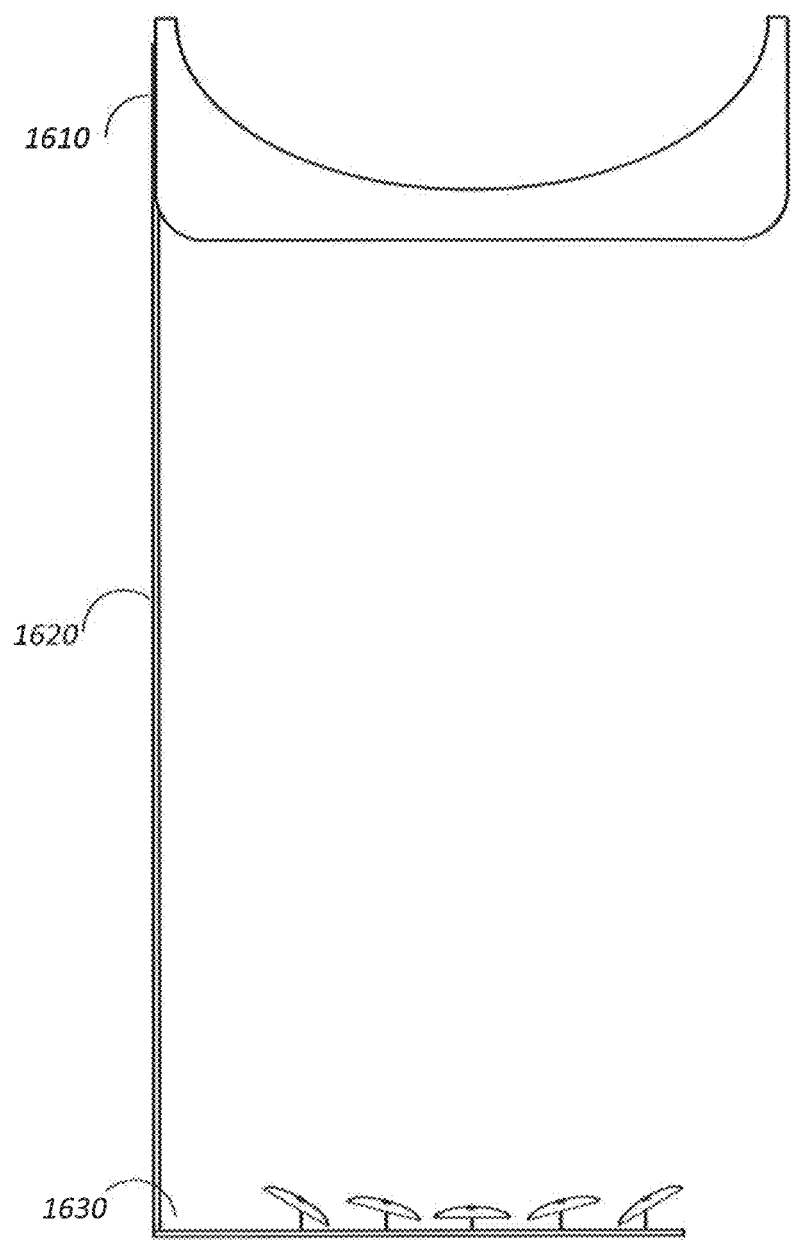
FIG. 6A is a partially diagrammatic view in elevation of Head Orientation Unit according to still another embodiment of the present invention in which multiple bubble levels are employed in arrays.
Figure 6B:
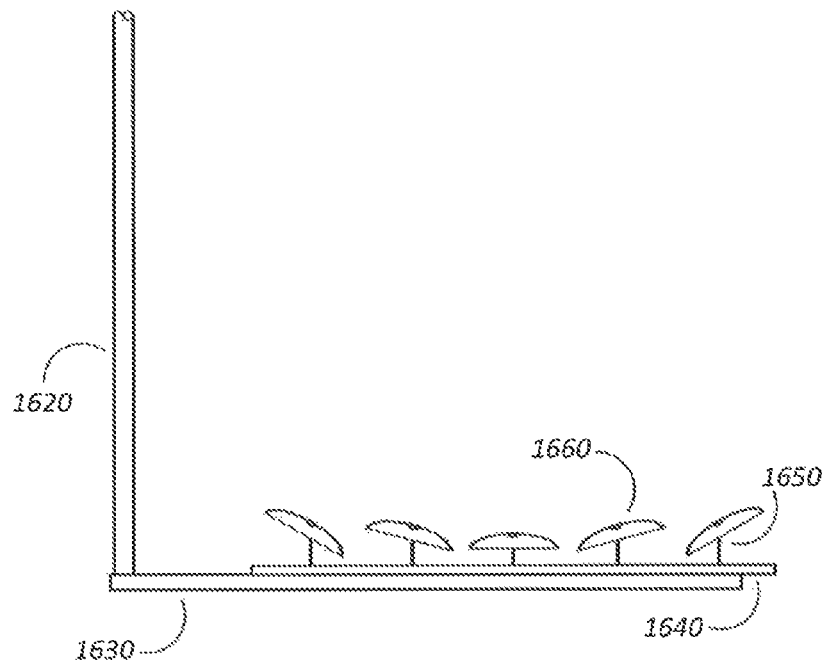
FIG. 6B is a partially diagrammatic view in elevation a head position display portion of the Head Orientation Unit of FIG. 6A.
Figure 6C:
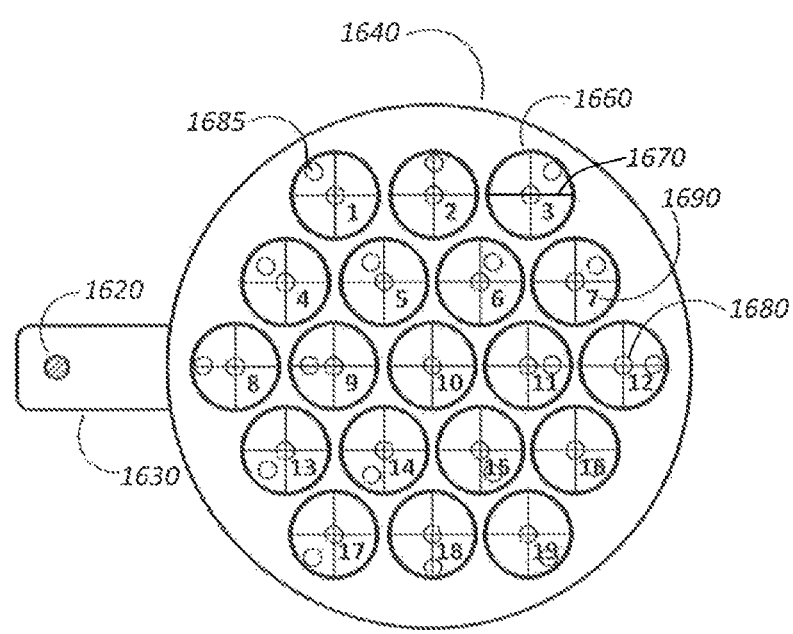
FIG. 6C is a top view in plan of a portion of the display of FIG. 6B.
Figure 6D:
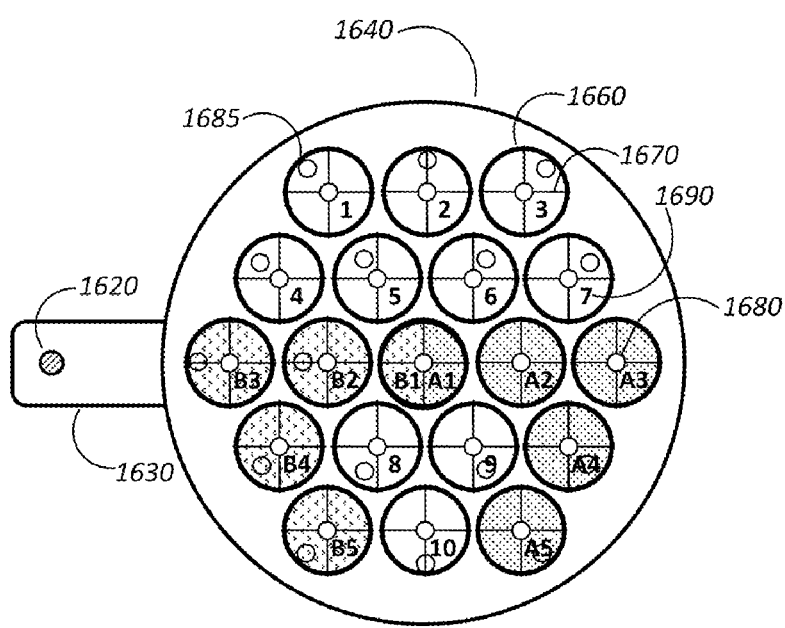
FIG. 6D is a top view in plan of the portion of the display of FIG. 6C but showing a predetermined path of head movement for the user during use of the system of the invention.
Figure 6E:
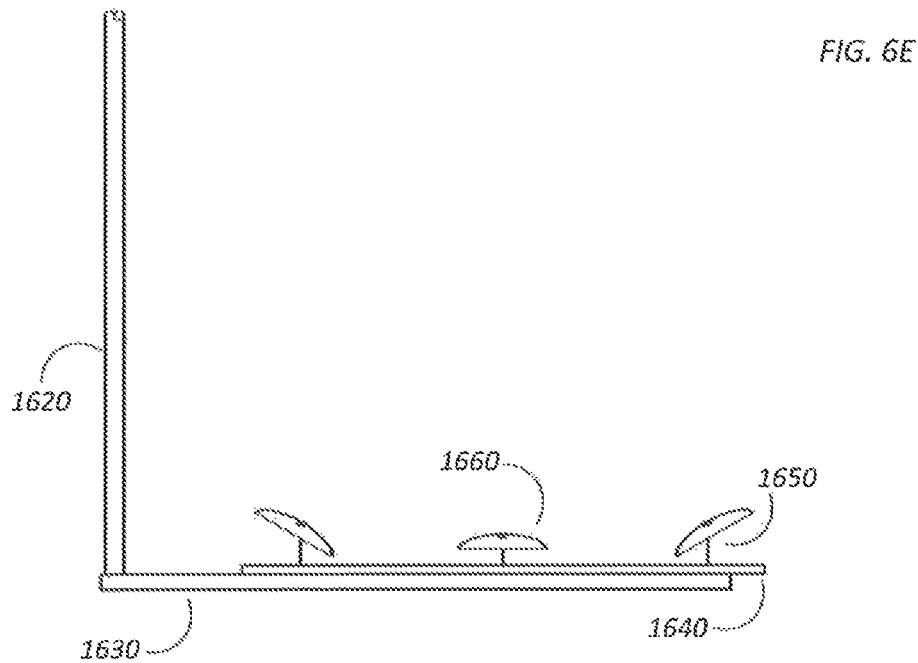
FIGS. 6E and 6F illustrate partial arrays of bubble levels.
Figure 6F:
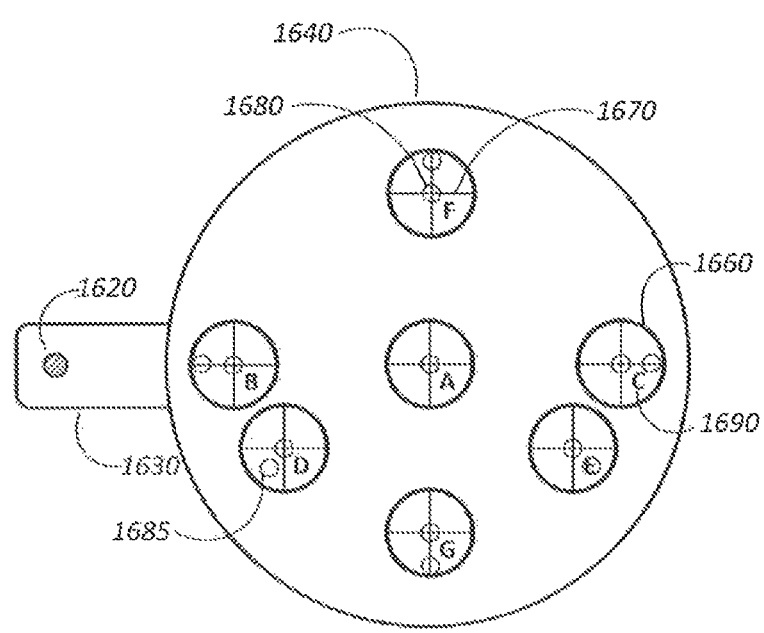

FIG. 6D illustrates two pre-defined paths of successive head orientations, the first designated by indicia A1 through A5 and the second designated by indicia B1 through B5. Each path can be easily seen and followed by having the bubble levels 1660 along that path marked by a different color. The central bubble level 1660 is marked "A1" and "B1" and has the color for the A1 through A5 path and the B1 through B5 path. For each of these two paths, the user starts at the center bubble level 1660. If the user is taking path A1 through A5, the user then moves his head until the bubble 1685 is centered in the bubble level 1660 designated by A2. Next the user moves his head until the bubble 1685 is centered in the bubble level 1660 designated by A3, etc. FIGS. 6B through 6D illustrate full arrays of bubble levels 1660. FIGS. 6E and 6F illustrate a partial array of bubble levels 1660.

Figure 7A:
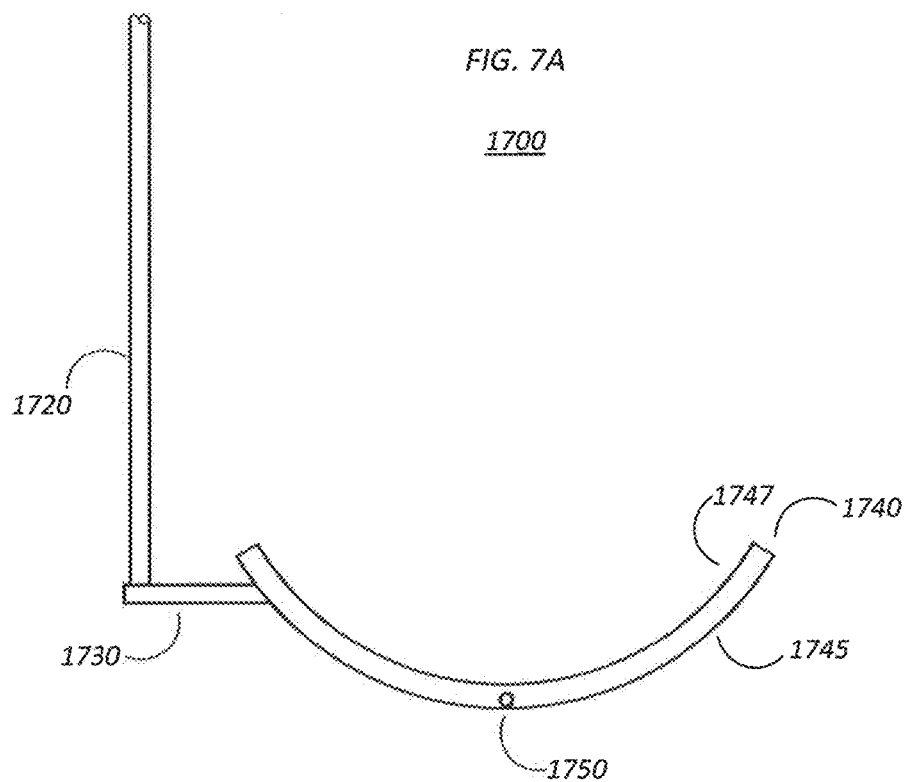
FIG. 7A is a partially diagrammatic view in elevation of an alternative Head Orientation Unit.
Figure 7B:
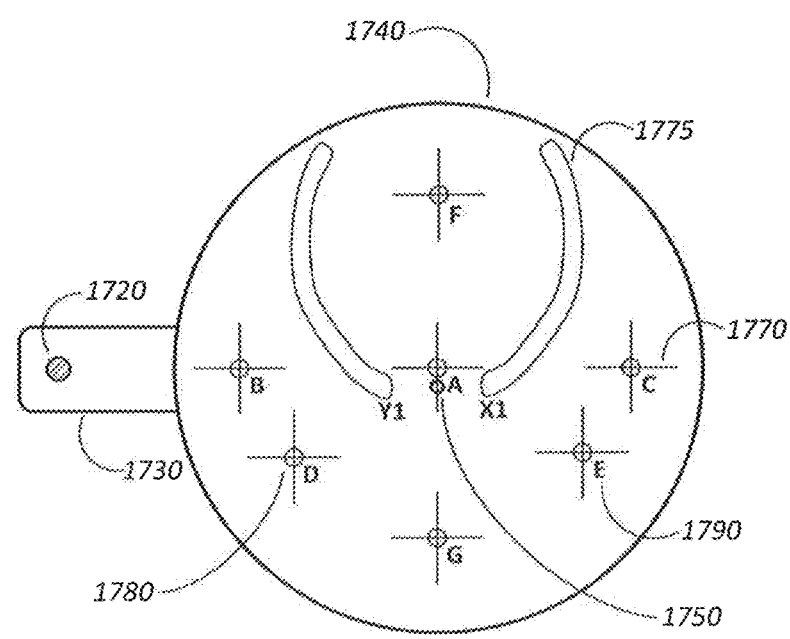
FIG. 7B is a partially diagrammatic top view in plan of the display of FIG. 7A.

FIGS. 7A through 7B show details of an alternative Head Orientation Unit 1700 comprising a head interface member (not shown in FIG. 7A for simplicity purposes) similar to members 1510 or 1910 (described below in relation to FIG. 9), a spacer arm 1720, display support arm 1730, and a ball-in-shell display unit comprising shell 1740 and rolling ball 1750. Hollow display shell 1740 contains ball 1750 between upper display shell 1747, lower display shell 1745 and an edge that separates and connects them. Ball 1750 can be, for example, be a small metal or glass ball, small enough to move easily inside display shell 1740. Aligning the location of the ball 1750 with the center of an alignment indicium 1780 corresponds to the user's head in a pre-defined orientation with respect to the vertical. Indicia 1790 on upper display shell 1747 (or lower display shell 1745) distinguish one alignment indicium from another. A path track indicium 1775 can be defined. The user starts with the ball 1750 at end "X1" of the path track indicium 1775, for example, and continues moving his head such that the ball 1750 stays within path track indicium 1775 until it reaches the opposite end of the path. The rate of movement of the user's head can be slowed by filling display shell 1740 with a fluid. The rate is higher with a lower viscosity liquid and lower with a higher viscosity fluid.

Figure 8C:
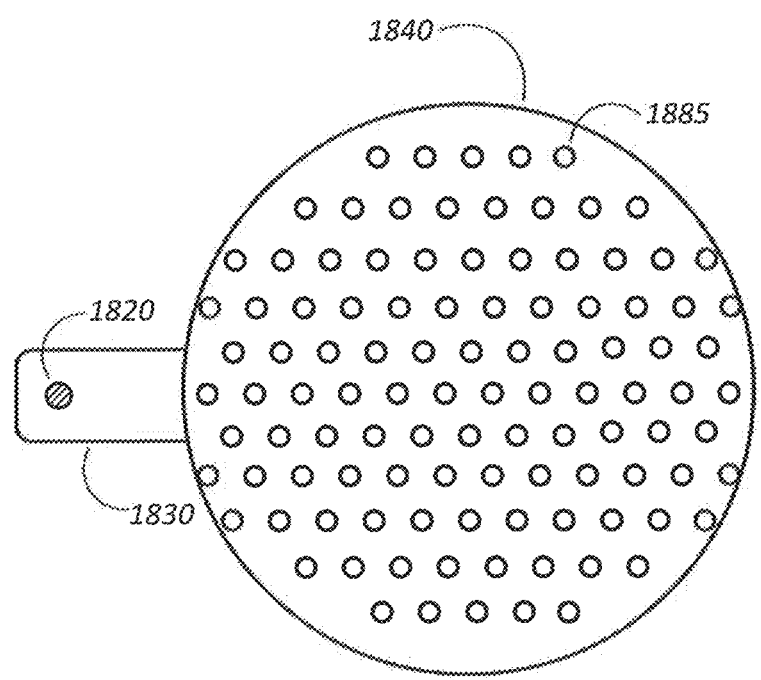
FIG. 8C is a partially diagrammatic top view in plan of an alternative embodiment the display of FIG. 8A.

FIGS. 8A and 8C relate to details of an alternative Head Orientation Unit 1800. Head Orientation Unit 1800 in FIGS. 8A and 8B comprises a head interface member (not shown in FIG. 8A for simplicity purposes) similar to members 1510 or 1910 (described below in relation to FIG. 9), a spacer arm 1820, display support arm 1830, display 1840, and display plumb pointer 1850. The display plumb pointer ring 1854 is at the top end of display plumb pointer 1850 and passes through a support ring 1856 that is affixed to one end of support ring arm 1822. The opposite end of support ring arm 1822 is affixed to spacer arm 1820, and between its ends to stabilizing arm 1824. The opposite end of stabilizing arm 1824 is affixed to display support arm 1830. The lower end of display plumb pointer 1850 is a pointer head 1852 that points to locations on the surface of display 1840. Aligning the location of the pointer head 1852 with the center of an alignment indicium 1880 corresponds to the user's head in a pre-defined orientation with respect to the vertical. Indicia 1890 on display 1840 distinguish one alignment indicium from another. A path track indicium 1875 can be defined. The user starts with the pointer head 1852 at end "Y1" of the path track 1875, for example, and continues moving his head such that the pointer head 1852 stays within path track 1875 until it reached the opposite end of the path track.

FIG. 8C illustrates an alternative display 1840 for Head Orientation Unit 1800 comprising a digital display, specifically an array of small LEDs 1885. The user selects a mode by a switch on the back or side of the display 1840. Each mode corresponds to a bathing mode for each specific head structure accessible via the nasal cavity or set of such structures. For example, there can be a mode for bathing the left maxillary sinus, one for the right maxillary sinus, one for the right frontal sinus, one for bathing the left olfactory bulb, etc. Each mode corresponds to a pattern of head orientations. To direct the user to the first head orientation for a specific mode, the LED associated with that orientation is lit by a battery. The user aligns the display plumb pointer 1850 to be above that LED. The program for that mode keeps this LED lit for a pre-defined time. Other LEDs are lit, in turn and each LED 1885 for a potentially different predetermined time. This process is repeated for each LED 1885 in the pre-defined path for the selected mode.

Another variant of the embodiment illustrated in FIG. 8C uses the display of a mobile device on a platform to replace display 1840. An app running on the mobile device can display one or a series of spots to direct the user to orient his head such that the display plumb pointer 1850 is aligned to the appropriate spot on the mobile device display at the proper time and for a pre-defined duration.

FIG. 9 pertains to details of another alternative Head Orientation Unit 1900 comprising a head interface member 1910, a spacer arm 1920, display support arm 1930, and a display 1940. Head interface member 1910 can be a set or pair of glasses or any other device that can be removably attached to the head. One end of spacer arm 1920 is affixed to head interface member 1910 and the other end is affixed to display support arm 1930. Display 1940 is affixed to display support arm 1930 and can be one of many displays such as 1800.

FIGS. 10A and 10B pertain to details of still other alternative Head Orientation Units 2000 comprising a mobile device 2030 (mobile phone, tablet, etc. shown in FIG. 10C), an app that runs on the mobile device with the ability to detect the mobile device orientation with respect to vertical, and a means to determine the orientation of the user's head with respect to the mobile device 2030. A camera in the mobile device can use the image of the user's head (or some part thereof) to determine the orientation of the user's head with respect to the mobile device via any of a number of methods known in the art. Alternatively, a LOID (Location and Orientation Identification) tag 2020 affixed to a pair of glasses 2010 worn by the user and observed by the camera of the mobile device 2030 can be used for the app to easily determine the orientation of the user's head with respect to the mobile device. Such LOID tag is described and illustrated in U.S. Pat. No. 8,471,812 (Bunch). By combining the orientation of the user's head with respect to the mobile device with the orientation of the mobile device with respect to vertical, it is simple for the app to compute the orientation of the user's head with respect to vertical. The app then communicates to the user visually via the mobile device display and/or aurally via the mobile device speaker as regarding which way the user should moves his head or to provide other directions for the use of the system. Because the mobile device 2030 is able to detect changes in its orientation with respect to the vertical while also detecting the orientation of the user's head with respect to the mobile device 2030, the mobile device can be held in the user's hand and still provide precise feedback to the user regarding the orientation of his head with respect to the prescribed orientation for the specific time for the specific preselected mode. The illustrated LOID can be used for the app to report in real time to the physician the identity of the user, and can also provide information as to which modes are used at what times. This permits the physician to monitor the proper use of the device and the app and/or the physician to correlate specific treatments to the results of the treatment.

FIGS. 11, 12, and 13A through 13C relate to details of other alternative pumps for the Fluid Agitation Unit.

FIG. 11 illustrates in detail to a low-cost alternate pump 3000 for the Fluid Agitation Unit 370. Alternative pump 3000 is powered by water pressure. Water pressure source connector 3065 is an elastomeric tube that stretches over the end of a faucet making a water-tight, pressure seal with the exterior of the faucet. When the faucet is turned on, a water flow limiter 3062 in inlet tube 3060 limits the rate of flow of the water into pressure container 3050 (and hence the flow of air out of pressure container 3050). Water flow limiter 3062 can be a small diameter orifice serving as a flow restrictor.

Water flows from the faucet through inlet tube 3060 extending through pressure-tight plug 3030 into pressure container 3050. The water flow forces the air in pressure container 3050 through outlet tubing 3080 extending through pressure-tight plug 3030. Male Luer lock 3075 at the end of tubing 3080 forms a fluid-tight seal with female Luer lock connector 350 on removable tip member 310.

Figure 12:
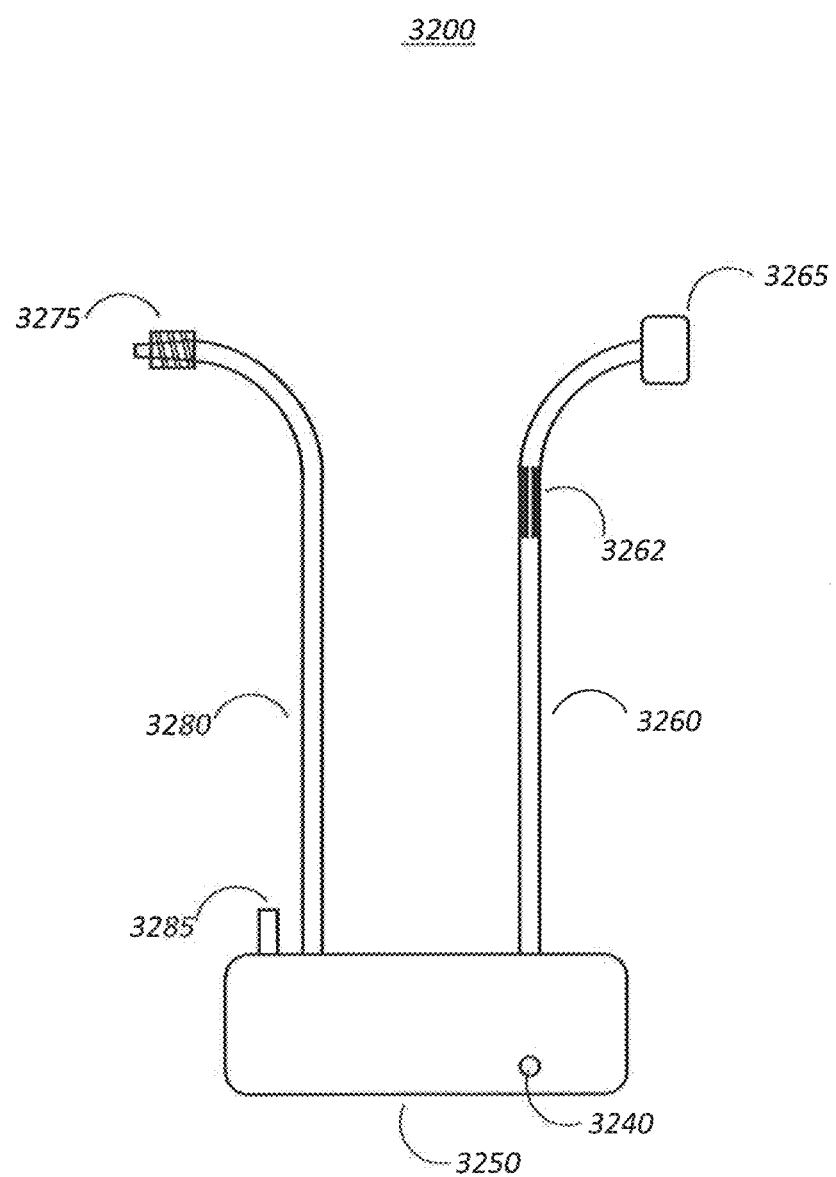
FIG. 12 is a diagrammatic view of another alternative pump that can be used in place of the pump for the Fluid Agitation Unit of FIG. 3C.

FIG. 12 relates in detail to a low-cost faucet-powered alternative pump 3200 for the Fluid Agitation Unit 370. Pump 3200 is a water-pressure powered, turbine air pump such as is known to the art. Water pressure source connector 3265 is an elastomeric tube that stretches over the end of a faucet making a water-tight, pressure seal with the exterior of the faucet. When the faucet is turned on, a water flow limiter 3262 in inlet tube 3260 limits the rate of flow of the water into water-pressure powered turbine in 3250. Water flow limiter 3262 can be a small diameter orifice. Water flows from the faucet through inlet tube 3260 into the turbine in pump housing 3250, rotating the turbine and then flowing out through outlet 3240. The turbine is coaxial with, and thus drives, an air pump that pumps air through outlet tubing 3280. Male Luer lock 3275 at the end of tubing 3280 forms a fluid-tight seal with female Luer lock connector 350 on removable head unit 310. Fresh air enters the pump via air inlet 3285.

A fourth alternative source of gas under pressure for the Fluid Agitation Unit 370 can come from devices for dispensing $CO_2$ from $CO_2$ cartridges such as commercially available beer dispensers.

A fifth source of pressurized gas can be a gas generated from a chemical reaction, such as $CO_2$ generated from the reaction of sodium bicarbonate and an acid, such as citric and/or acetic acid in a pressure-tight container with a tube that connects to removable tip member 310.

Another alternative is for the gas-generating chemical reaction to occur in the fluid column supported by the Fluid Introduction and Retention Unit. In one embodiment an effervescent tablet, granules and/or powder can be added to the bathing fluid in syringe 260 before the fluid is introduced into the nasal cavity and/or sinuses. The solids can be preinstalled in syringe 260 and the fluid added just before use. The solids can be a mixture of solid sodium bicarbonate and citric acid and the fluid can be water. Alternatively, the fluid can be an acidic solution of, for example, citric and/or acetic acid and the solid can be sodium bicarbonate. Alternatively, the fluid can be a solution of sodium bicarbonate and the solid can be citric acid.

Figures 13A, 13B, 13C:
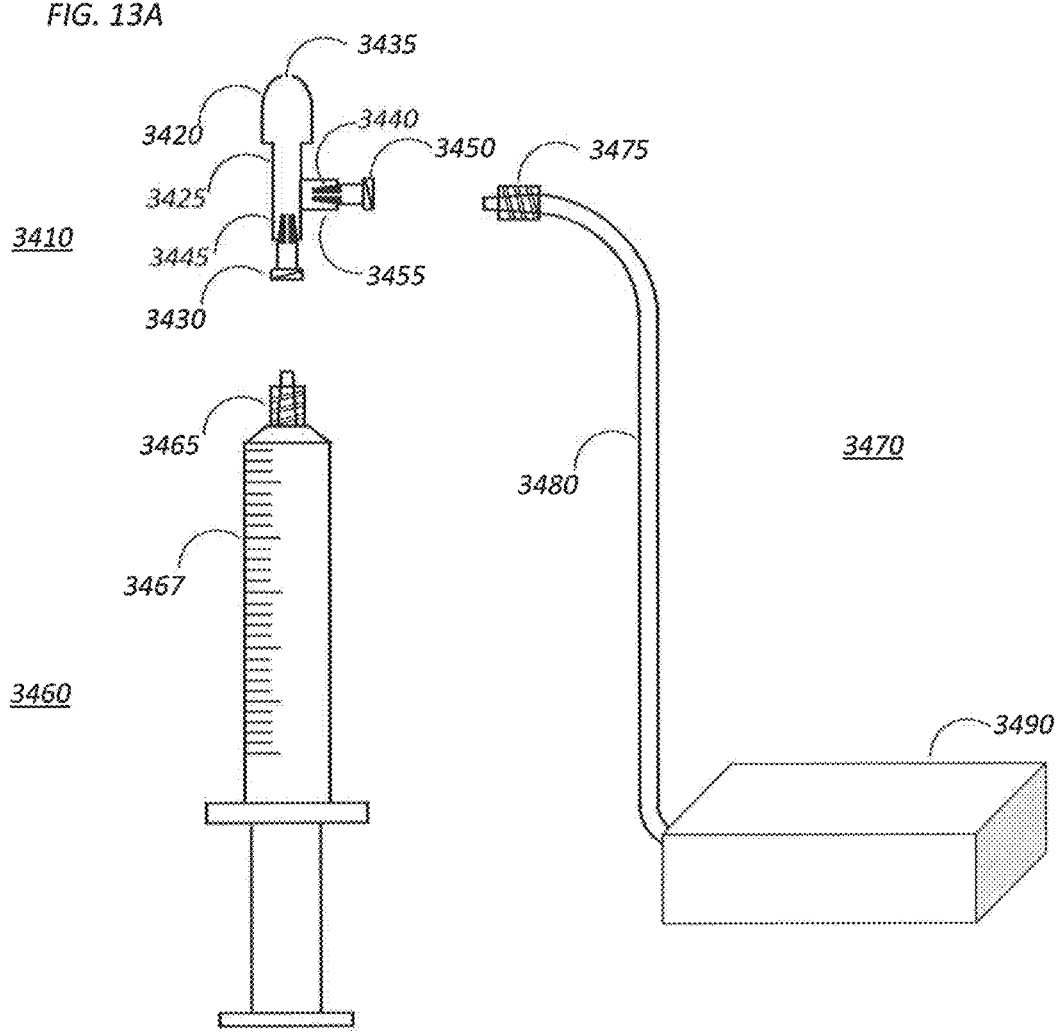
FIGS. 13A, 13B and 13C are partially diagrammatic views in elevation of an alternative removable tip member and a syringe, respectively, and an alternative Fluid Agitation Unit.

FIGS. 13A through 13C relate to details of an alternative Fluid Agitation Unit 3470 for introducing fluids into the removable tip member 3410 forming part of Fluid Introduction and Retention Unit 3400. Male Luer lock member 3475 at the end of tubing 3480 forms a fluid-tight seal with female Luer lock connector 3450 on removable tip member 3410. The other end of tubing 3480 is affixed to battery-powered air pump 3490. The tip member 3410 is similar to tip member 310 (FIG. 3A) and includes a nostril interface 3420, a tubular body 3425 with a female Luer connector 3430 that engages male Luer connector 3465 on the syringe, a channel or through bore 3435, an optional one-way valve 3445, an additive inlet port 3440 provided with a female Luer lock connector 3450 that connects to male Luer lock member 3475 at the end of tubing 3475, and an optional one-way valve 3455 in inlet port 3440.

FIGS. 14A through 14F, FIGS. 15A and 15B, and FIGS. 16A and 16B relate to alternative nozzles for Fluid Introduction and Retention Units.

FIGS. 14A through 14F relate to alternative nozzles for Fluid Introduction and Retention Units. FIG. 14A illustrates alternative nozzle 4400 used with Fluid Introduction and Retention Unit 5000A, a variant of Fluid Introduction and Retention Unit 5000 described in greater detail in relation to FIG. 18 below. In Fluid Introduction and Retention Unit 5000A, outlet arms 5020 both connect directly to the single nozzle 4400, whereas in Fluid Introduction and Retention Unit 5000 each of the two outlet arms 5020 is connected directly to a separate nozzle. The direct connection of both outlet arms 5020 to the single nozzle 4400 is assisted by an optional narrow extension 5035.

FIG. 14B illustrates alternative nozzle 4400 used with Fluid Introduction and Retention Unit 5200A, a variant of Fluid Introduction and Retention Unit 5200 described in greater detail in relation to FIGS. 19A through 19O and the description thereof below. In Fluid Introduction and Retention Unit 5200A outlet arms 5222 both connect directly to the single nozzle 4400 whereas in Fluid Introduction and Retention Unit 5200 each of the two outlet arms 5222 is connected directly to a separate nozzle. The direct connection of both outlet arms 5222 to the single nozzle 4400 is assisted by an optional narrow extension 5235.

FIG. 14C illustrates the side view of alternate nozzle 4400. Nozzle 4400 supports the flow of fluids into and out of the nasal cavity via a single nozzle. Fluids can flow into the nasal cavity via one or multiple outlets 4430 and return via one or more inlets 4420. The fluids flow into nozzle 4400 from a Fluid Introduction and Retention Unit, such as 5200A, through female Luer 4470. The fluids flow out of nozzle 4400 back into a Fluid Introduction and Retention Unit, such as 5200A, through female Luer 4460. FIG. 14D illustrates a cross-section of a variant of nozzle 4400 wherein the outlets 4300 are parallel to the axis of nozzle 4400. The channels for outlets 4430 are connected to one another and to the channel for female Luer 4470 via toroidal channel 4432. Because the fluids are removed from the nasal cavity through the same nozzle 4400 from which they entered the nasal cavity, the flow can be continuous and at a high rate. This rapid flow can generate turbulence to assist the fluids entry into the sinuses. If the rate of flow out of the nasal cavity is kept equal to the flow into the nasal cavity, the volume of fluid in the nasal cavity can be kept constant. The flow rates can be kept constant by the input and output flows being driven by the same pump. Such a pump can, for example, be a battery-powered peristaltic pump in the Fluid Introduction and Retention Unit, such as unit 5400 illustrated in FIGS. 21A through 21D and described below. First the flow is introduced into the nasal cavity by pressing spring-loaded peristaltic motor switch 5490. The flow rate is kept low by pressing only gently on switch 5490 as detailed in the description of unit 5300. After the nasal cavity is full, the flow out of the nasal cavity is begun by rocking lever 5426 forward. This engages the tube that pumps the fluid out of the nasal cavity. The direction of flow can be reversed by pressing button 5444 as detailed in the description of unit 5300. This reverses the current in the DC motor that drives the peristaltic pump. When the process is completed, the inlet pump can be disengaged by releasing spring-biased peristaltic motor switch 5490, causing the nasal cavity to be neatly drained. Then the fluids enter the nasal cavity through outlets 4420 and exit the nasal cavity through outlets 4430.

FIG. 14E illustrates a cross-section of a variant of nozzle 4400 wherein the outlets 4435 converge and are not parallel to the axis of nozzle 4400. This can increase the turbulence in the fluid flow inside the nasal cavity. The rate of fluid flow in and out of one or more nozzle holes into and from the nasal cavity can together or at least partially independently vary according to a pre-specified, random or pseudo-random pattern to introduce additional turbulence. The liquid can flow in through one or more of the holes while the air (for added turbulence) can flow in through one or more other holes. The channels can be at various angles with respect to one another to produce clashing streams. For all embodiments, particles of one or more sizes and mixed into the fluid can assist in cleaning the bathed nasal cavity structures and/or sinuses.

FIG. 14F illustrates a cross-section of a variant of nozzle 4400 with an energy transducer 4450 which can transmit energy to the nasal cavity. This energy is useful for many purposes, including but not limited to the treatment of illness or for diagnostic purposes. The energy can be of any form including sound, such as mechanical vibration, infrasound, audible sound and/or ultrasound. Such energy can be non-ionizing radiation such as electromagnetic radiation including radiant heat, UV, visible light, radio waves, and/or microwaves, etc., and/or static and/or changing electric, magnetic, and/or electromagnetic fields.

FIGS. 15A, 15B and 16A, 16B relate in detail to alternative nozzles for Fluid Introduction and Retention Units.

FIGS. 15A and 15B illustrate a Fluid Introduction and Retention Unit adapted for use with mechanically induced turbulence nozzles 4600 and 4700. Mechanical Drive Unit 4770 is removably attachable to syringe 360 via clips 4775 affixed to the body 4777 of Mechanical Drive Unit 4770. At least the ends of clips 4775 are clear so that the indicia on syringe 360 can be easily seen. A motor inside the body 4777 drives shaft 4774. Driver drive wheel 4773 is affixed to the opposite end of drive shaft 4774. Arm 4772 extends from body 4777 to hold driver alignment plate 4771. Driver alignment plate 4771 has a slot into which nozzle alignment plates 4662 or 4762 on nozzles 4600 or 4700 are inserted. The alignment of driver alignment plate 4771 with nozzle alignment plate 4662 or 4762 helps to ensure that the driver drive wheel properly aligns with nozzle drive wheel 4626 or 4726. The user employs switch 4776 to turn the battery-powered electric motor on or off when desired.

FIG. 16A illustrates in detail a cross-section of mechanically induced turbulence nozzle 4600. Female Luer connector 4654 on the lower end of nozzle input tube 4652 screws into male Luer lock 365 on syringe 360, attaching mechanically induced turbulence nozzle 4600 to syringe 360. The upper end of nozzle input tube 4652 directs the flow of fluids into the turbulence chamber 4628. Inner shell 4620 defines most of the turbulence chamber 4628. Driver drive wheel 4773 drives nozzle drive wheel 4626 at the lower end of shaft 4624. Shaft 4626 has turbulence propeller 4622 affixed to its upper end. The spinning of turbulence propeller 4622 creates turbulence in the lower portion of the fluid column in the nasal cavity via opening 4634. This turbulence helps to drive the fluid into the sinuses. Outer shell 4610 abuts the outside of the nasal opening to prevent the fluid column from escaping. Input tube 4652 supports shaft 4624 and prevents the escape of the fluids. Shell structure 4632 attaches outer shell 4610 to the mid portion of inner shell 4620. Structure 4664 extends from the surface of nozzle alignment plate 4662 and mates with a slot in and perpendicular to the main slot in driver alignment plate 4771 and helps to restrict motion between them.

FIG. 16B illustrates in detail a cross-sectional view of mechanically induced turbulence nozzle 4700. Female Luer connector 4754 on the lower end of nozzle input tube 4752 screws into male Luer lock 365 on syringe 360, attaching mechanically induced turbulence nozzle 4700 to syringe 360. The upper end of nozzle input tube 4752 directs the flow of fluids into the turbulence chamber 4728. Inner shell 4720 defines most of the turbulence chamber 4728. Driver drive wheel 4773 drives nozzle drive wheel 4726 at the lower end of flexible shaft 4725 to shaft 4724. Arm 4730 supports the lower portion of shaft 4725. Arms 4744 support the 4724. Turbulence propeller 4722 is affixed to the upper end of shaft 4724. The spinning of turbulence propeller 4722 creates turbulence in the lower portion of the fluid column in the nasal cavity via opening 4734. This turbulence helps to drive the fluid into the sinuses. Outer shell 4710 abuts the outside of the nasal opening to prevent the fluid column from escaping. Grommet seal 4736 allows shaft 4725 to turn while preventing the escape of the fluid.

Figure 17B:
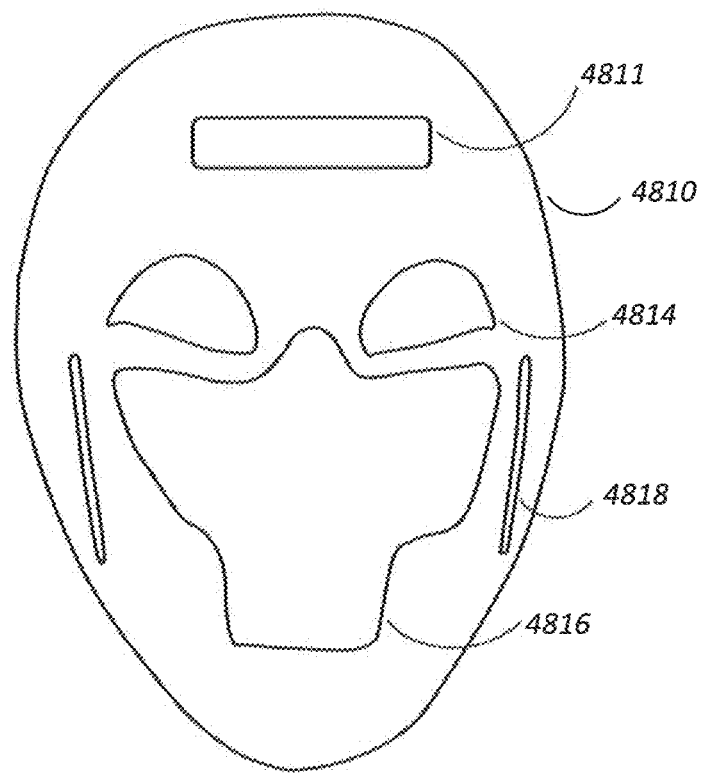
Figure 17C:
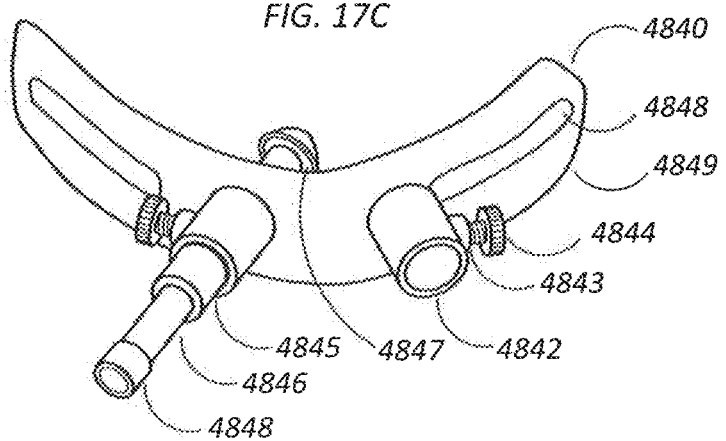

FIGS. 17A through 17C relate in detail to an alternative Fluid Introduction and Retention Unit 4800. It is important to visualize the results of sinus surgery. This can be done using a Fluid Introduction and Retention Unit to introduce fluids into the sinuses while the patient is in an MRI unit. The MRI shows fluids in the sinuses when present. In an MRI unit, the patient must lay with his arms at his side. However, this prevents the patient from holding other Fluid Introduction and Retention Units in contact with the entrance of the nasal cavity. To resolve this problem, a hands-free Fluid Introduction and Retention Unit is provided in accordance with another aspect of the invention. FIG. 17A illustrates an overview of the hands-free Fluid Introduction and Retention Unit which comprises a mask subsystem 4810, a nozzle assembly support structure 4840, and optional head support 4820. Nylon bolts 4830 and nylon wing nuts 4835 hold mask subsystem 4810 and a nozzle assembly support structure 4840 together. FIG. 17B illustrates the mask subsystem 4810 of hands-free Fluid Introduction and Retention Unit 4800. Mask subsystem 4810 is a plastic mask held to the patient's head by an elastic strap. Eye holes 4814 permit the patient to see. Cutout 4816 provides access to the nose by the nozzle assembly support structure 4840. Each vertical slot 4818, one on each side of the mask 4810, and its corresponding horizontal slot 4848 permit great flexibility in the location and orientation of nozzle 4847. Nylon bolts 4830 pass from the inside of vertical slots 4818 in each side of mask 4810. Each nylon bolt 4830 then passes through a horizontal slot 4848 in the nozzle assembly support structure 4840. A nylon wing nut 4835 hand tightened on each nylon bolt 4830 holds nozzle assembly support structure 4840 tightly to mask subsystem 4810 such that the location and orientation of nozzle 4847 is optimal for the patient's comfort and to prevent the outward flow of the sinus bath fluids. Velcro tape strip 4811 mates to another Velcro tape strip on optional head support 4820. Head support 4820 supports the patient's head while laying face down on the MRI's table. This improves the patient's comfort and helps to keep the patient's head still during the MRI scan.

The nozzle assembly support structure main body 4849 is flexible, increasing the ability to adjust the nozzle assembly support structure to each specific user. Rigid plastic support tube 4842 is affixed to the nozzle assembly support structure main body 4849 and aligns and supports rigid nozzle extension tube 4845 with respect to main body 4849. Nylon screw 4844 is used to adjust the extension of the nozzle 4847 with respect to main body 4849. Nylon screw 4844 screws into 4843, a rigid threaded part of plastic support tube 4842. Nylon screw 4844 extends through threaded piece 4843 to contact nozzle extension tube 4845. Loosening nylon screw 4844 a little allows nozzle extension tube 4845 to slide freely (though snugly) in plastic support tube 4842. Tightening nylon screw 4844 prevents nozzle extension tube 4845 from sliding in plastic support tube 4842, thereby locking its location and orientation.

Flexible plastic tube 4846 slides freely (though snugly) in rigid plastic support tube 4842. Rigid plastic nozzle 4847 has a tube coaxial to and in the back of the nozzle. The outside of that tube forms a fluid tight seal with the inside of flexible plastic tube 4846 by friction fit. Nozzle 4847 at one end of flexible plastic tube 4846 prevents that tube from sliding away from the user's nose. In the opposite end of flexible plastic tube 4846 is adapter 4848. Adapter 4848 permits a friction-fit, fluid tight connection between flexible plastic tube 4846 and longer, flexible plastic tubing that, in turn, attaches to a syringe such as 360 or the like. The user or physician controls the flow of the fluid into the sinuses.

FIG. 18 illustrates a double-nozzle Fluid Introduction and Retention Unit 5000 deployed at nostrils 5010 of a user's nose. Two nozzle support arms 5022 are affixed to a main body 5030. Each nozzle support arm provides a path for fluid flow to, and the support of, a nozzle 5022. Each nozzle 5022 forms a fluid-tight seal with a user's nostril 5010. The use of fluid-tight seals with both nostrils permits the irrigation and bathing of the nasal cavity and the sinuses using negative pressure. Here fluid is pulled up into one nostril by a negative pressure applied to the other nostril. The fluid enters main body 5030 through tube 5042 and exits main body 5030 through tube 5044. The negative pressure can be applied via tube 5044 or from within main body 5030 via a peristaltic pump, for example. The pump simultaneously provides a positive pressure to the other nostril. The negative and/or positive pressures applied to one or both nostrils, together and/or separately, can be varied.

Figure 19E:
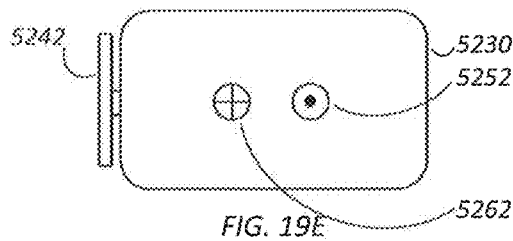
FIGS. 19A through 19O diagrammatically illustrate an alternative reversible flow, double-nozzle Fluid Introduction and Retention Unit according to the invention.
Figure 19J:
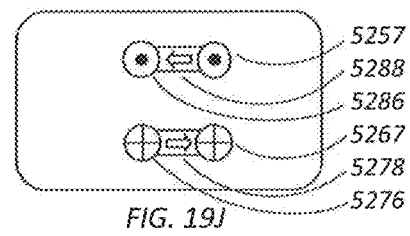
Figure 19F:
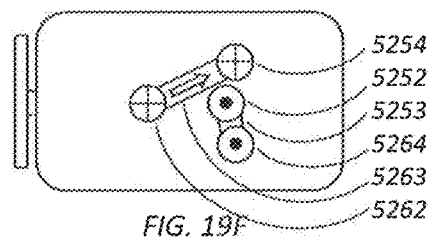
Figure 19K:
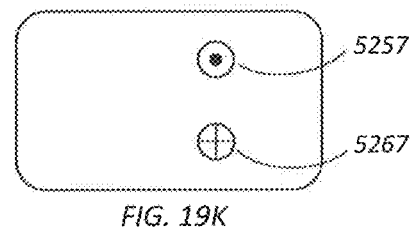
Figure 19G:
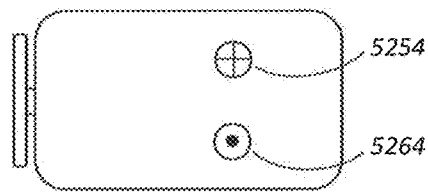
Figure 19L:
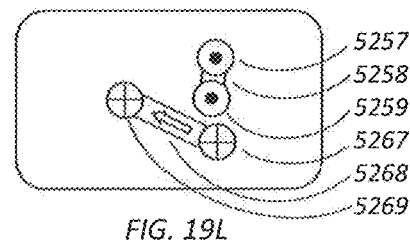
Figure 19H:
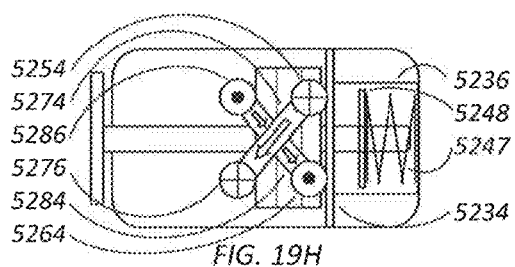
Figure 19M:
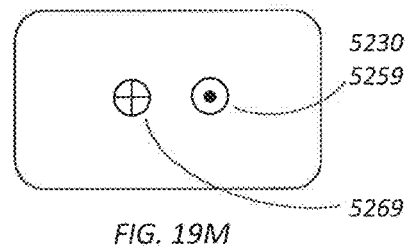
Figure 19I:
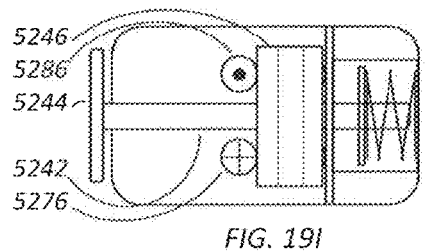
Figure 19N:
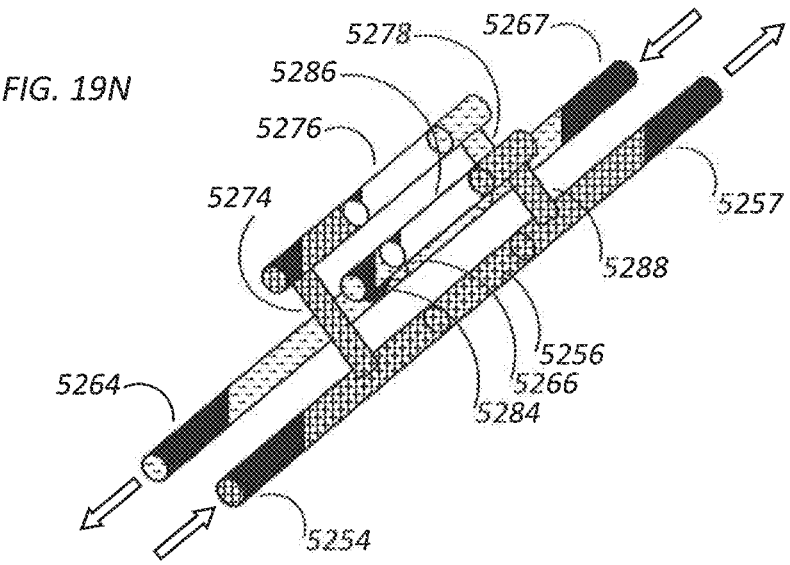
Figure 19O:
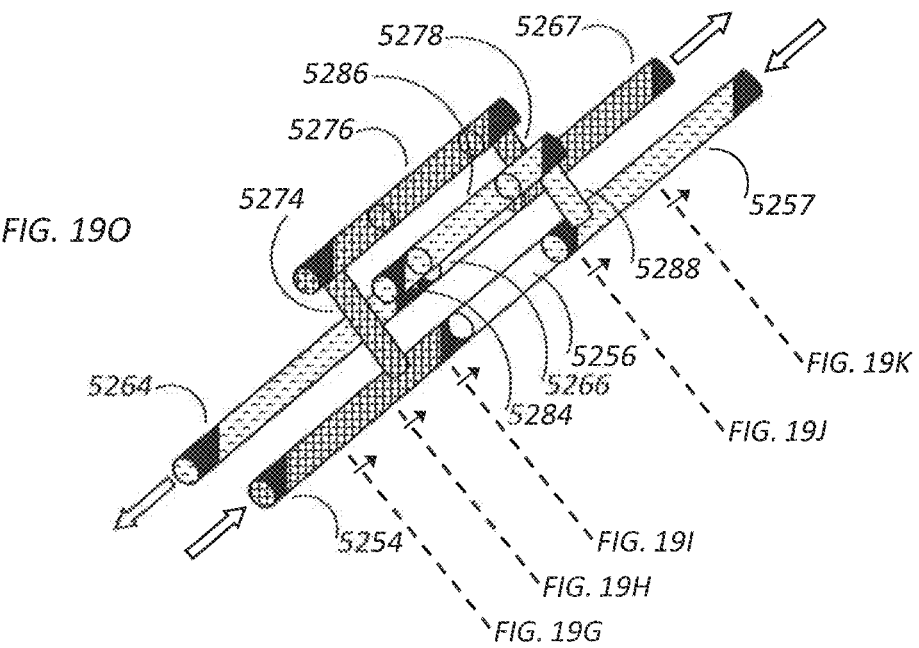

FIGS. 19A through 19O illustrate in detail a double-nozzle Fluid Introduction and Retention Unit 5200; FIGS. 19A through 19D illustrate the user's view of the deployed Fluid Introduction and Retention Unit 5200; FIGS. 19E through 19M illustrate details in sectional views taken at locations indicated in FIG. 19D; FIGS. 19N and 19O schematically illustrate the fluid flow circuit in the unit.

More specifically, a spring-biased actuator button 5244 is at the distal or external end of a rod 5242. Rod 5242 passes through and is rigidly affixed to tube block 5284. A spring block 5248 is rigidly affixed to and proximate the internal end of rod 5242. A spring 5247 is contained at one end by the inner wall of a main body 5230 and at the opposite end by spring block 5248. The internal end of rod 5242 also helps to keep spring 5247 in place. Rod 5242 is constrained to linear motion by passing through an aperture in each rod support 5232 and 5234. Rod supports 5232 and 5234 are affixed at both ends to the inner wall of main body 5230.

When button 5244 is not pressed, spring 5247 applies force to spring block 5248 and thus to rod 5242 and tube block 5246. This force is applied to tube block 5246 and is sufficient to pinch elastic tubes 5276 and 5286 against rod support 5232 sufficiently to prevent the flow of fluids through the tubes. Elastic tubes 5256 and 5266 are not pinched by tube block 5246 and, therefore, fluids are free to flow through them.

When button 5244 is pressed, overcoming the bias force applied by spring 5247, tube block 5284 pinches elastic tubes 5256 and 5266 against rod support 5234, preventing flow of fluids through them. Likewise, elastic tubes 5276 and 5286 are not pinched by tube block 5246, and fluids are free to flow through them.

Tube 5262 transports fluid into Fluid Introduction and Retention Unit 5200, and tube 5252 transports fluids out of the unit. When button 5244 is not pressed, the fluid flows into the user's nose via tube 5222 and out of the nose via tube 5226. When button 5244 is pressed, the fluid flows out of the nose via tube 5222 and into the nose via tube 5226. Thus, pressing button 5244 reverses the flow to the nose. Releasing button 5244 reverses the flow again. Repetitively pressing and releasing button 5244 in rapid succession causes the fluid to flow into a nostril, then out, then back in again, then back out in rapid succession. This process induces turbulence that helps to the direct sinus bathing fluid into the sinuses. While the fluid changes direction in tubes 5222 and 5226, the direction of flow in tube 5262 and tube 5252 remains constant.

FIGS. 19C through 19O illustrate the fluid circuit structures inside of Fluid Introduction and Retention Unit 5200. FIG. 19N is a view of the fluid circuit illustrated in FIG. 19C rotated 90° clockwise. FIG. 19O is a view of the fluid circuit illustrated in FIG. 19D rotated 90° clockwise. As also illustrated in FIGS. 19E, 19F, and 19G, independent of the state of button 5242, the fluid flows into Fluid Introduction and Retention Unit 5200 via tube 5262, then through tube 5263, then through tube 5254.

FIGS. 19C and 19N illustrate the fluid circuit structures and the flow of fluids inside of Fluid Introduction and Retention Unit 5200 when button 5242 is not pressed. When button 5242 is not pressed, the fluid flows from tube 5254 through elastic tube 5256, then through tube 5257, then tube 5259, then into tube 5222, through nozzle 5224, and into nostril 5212. In this mode, tube block 5246 prevents the fluid from tube 5254 from flowing through elastic tube 5276, ultimately preventing it from flowing into tube 5226. In this mode, fluid flows from nostril 5214 through nozzle 5228, then through tube 5226, then through elastic tube 5266, through tube 5264, out of body 5230 through tube 5252.

FIGS. 19D through 19M and 19O illustrate the fluid circuit structures and the flow of fluids inside of Fluid Introduction and Retention Unit 5200 when button 5242 is pressed. FIG. 19O is a view of the fluid circuit illustrated in FIG. 19D rotated 90° clockwise. As illustrated in FIGS. 19A and 19D, fluid flows into Fluid Introduction and Retention Unit 5200 via tube 5262. When button 5242 is not pressed the fluid flows from tube 5254 through tube 5274, then through elastic tube 5276, then tube 5278, then into tube 5267, through tube 5268, through tube 5269 to tube 5226 through nozzle 5228 and into nozzle 5214. In this mode, tube block 5246 prevents the fluid from tube 5254 from flowing through tube 5256, ultimately preventing it from flowing into tube 5222. In this mode, fluid flows from nostril 5212 through nozzle 5224, then through tube 5222, into 5230 through tube 5259, then through tube 5258, through tube 5257, through tube 5288, through elastic tube 5286, through tube 5284, through tube 5264, through tube 5253, then out of body 5230 through tube 5252.

FIGS. 20A and 20B illustrate a double-nozzle Fluid Introduction and Retention Unit 5300, which is a version of Fluid Introduction and Retention Unit 5200 with a built-in peristaltic pump. Pressing on spring-biased peristaltic motor switch 5390 turns on peristaltic pump motor 5394. Its spring (not illustrated) is much weaker than spring 5348 and thus the peristaltic pump motor is turned on without depressing button 5344. Fluid flows into main body 5330 through tube 5362 into the elastic peristaltic pump input path tube 5395. The fluid flows out of peristaltic pump input path 5395 to tube 5391. Fluid flows into peristaltic elastic pump output path tube 5396 from tube 5398. The fluid flows from the peristaltic pump output path 5396 out of main body 5330 through tube 5352. Battery-powered motor 5394 (batteries not illustrated) turns clockwise driving pump arms 5393. Peristaltic pump wheels 5392 and 5397 are mounted on the ends of peristaltic driving pump arms 5393. Pump wheels 5392 and 5397 squeeze elastic tubes 5395 and 5396 against the inner wall of the peristaltic pump shell pushing the fluids through elastic tubes 5395 and 5396. To operate only on positive pressure, the peristaltic elastic pump output path tube 5396 can be eliminated. To operate only on negative pressure, the peristaltic elastic pump input path tube 5395 can be eliminated.

Figure 21C:
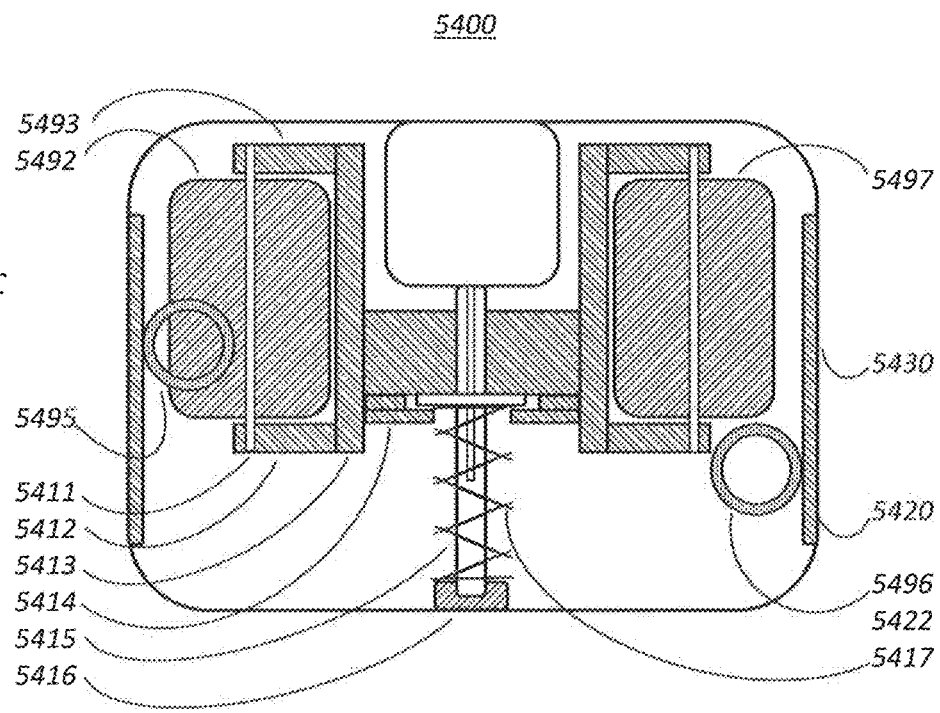
Figure 21D:
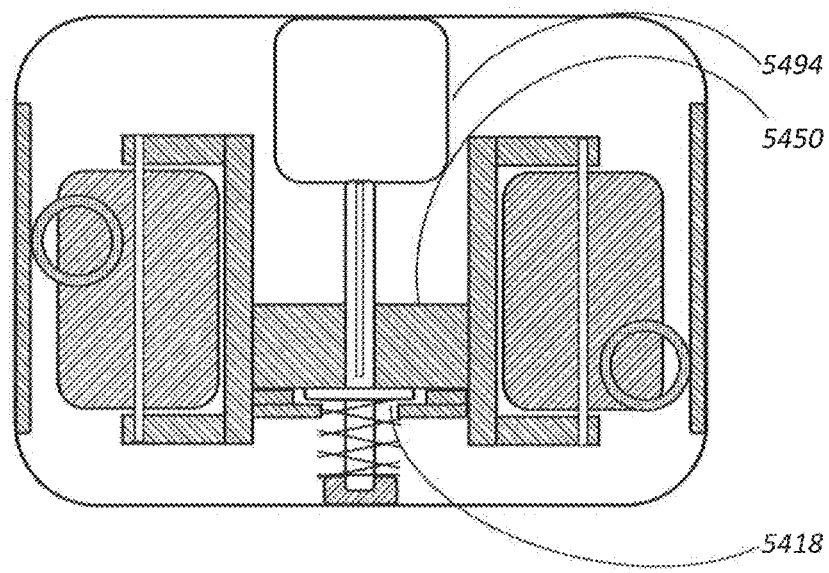

FIGS. 21A through 21D illustrate in detail a Fluid Introduction and Retention Unit 5400, which internally is a superset of Fluid Introduction and Retention Unit 5300 with means to selectively activate and deactivate the pumping of fluid out of the nasal cavity. The use of Fluid Introduction and Retention Unit 5400 is described above. Pressing on spring-loaded peristaltic motor switch 5490 turns on the peristaltic pump motor 5494. Fluid flows into main body 5430 through tube 5444 into the elastic peristaltic pump input path tube 5495. Fluid flows from the peristaltic pump output path 5496 out of main body 5430 through tube 5442. Battery-powered motor 5494 (batteries not illustrated) turns clockwise driving pump arms 5450. Peristaltic arm assembly is comprised of arms 5450, a mounting plate 5413 affixed at end of each arm 5450. Affixed to each plate 5413 is a pair of end plates 5412's that support respective axles 5411. One axle 5411 supports and allows pump wheel 5292 to turn freely, the other axle 5411 supports and allows pump wheel 5497 to turn freely. Peristaltic pump input path tubes 5495 and 5496 are not coplanar. Thus, when a rocker 5426 is in the orientation illustrated in FIG. 21A, peristaltic pump wheels 5492 and 5497 mounted on the ends of peristaltic driving pump arms 5494 engage only pump input path tube 5495 when the unit is in the mode illustrated in FIG. 21C. When the rocker 5426 is pressed forward as illustrated in FIG. 21B, a wire affixed to a piston 5418 pulls piston 5418 downward. The piston 5418 does not turn with respect to main body 5430. As piston 5418 is pulled down, it engages with annular plate 5414 and thus pulls the entire peristaltic pump arm assembly down against spring 5417, causing peristaltic pump wheels 5492 and 5497, mounted on the ends of peristaltic driving pump arms 5497, to engage pump input path tube 5495 and pump output path tube 5496 and the unit is in the mode illustrated in FIG. 21D. Pump wheels 5492 and 5497 squeeze elastic tubes 5495 and 5496 against the inner wall of the peristaltic pump shell 5420 pushing the fluids through elastic tubes 5495 and 5496. Peristaltic pump motor 5494 drives shaft 5415. As illustrated, the upper part of shaft 5415 has a cross-section shaped like a "plus" sign. Arm 5450 fits on the outside of that "plus" sign configuration such that shaft 5415 drives arm 5450, but arm 5450 can easily slide up and down on shaft 5415. FIG. 21C illustrates spring 5417 pushing the entire peristaltic arm assembly upwards.

Figure 22C:
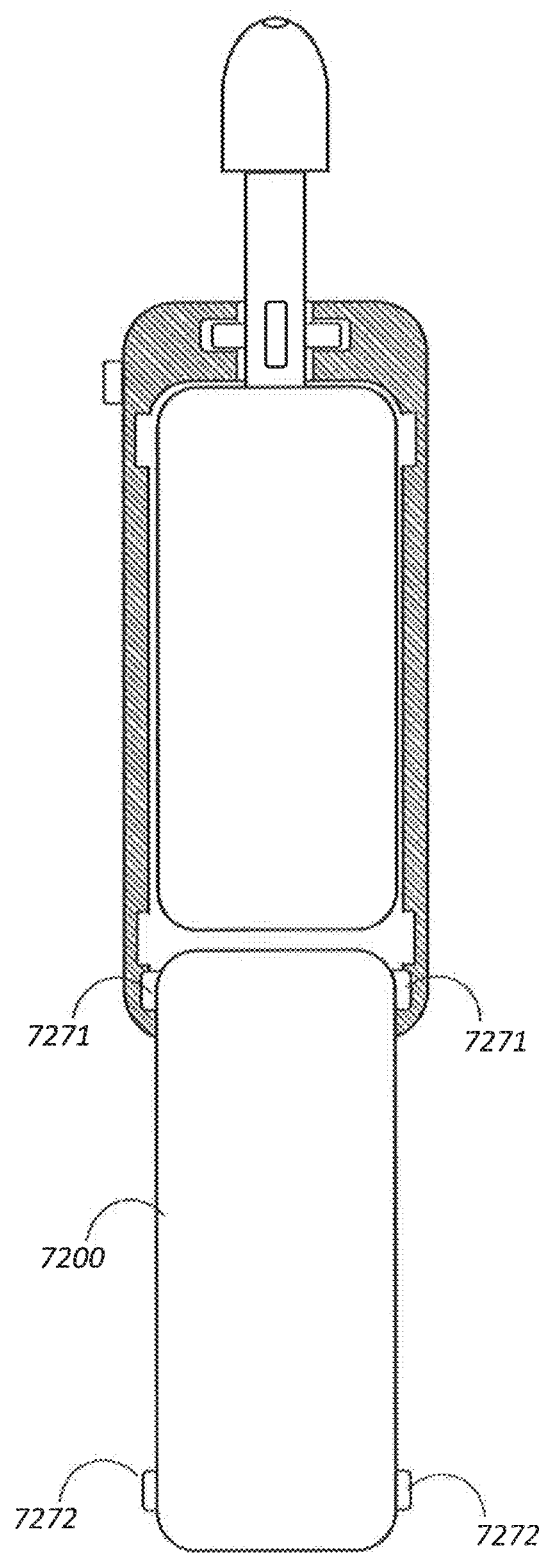
FIGS. 22A through 22O diagrammatically illustrate a Fluid Introduction and Retention Unit utilizing a pre-filled fluid cartridge.
Figure 22F:
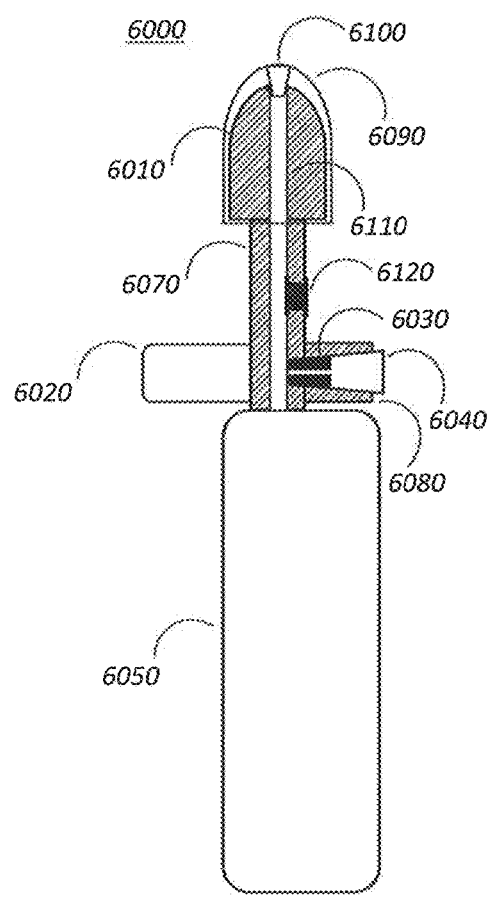
Figure 22G:
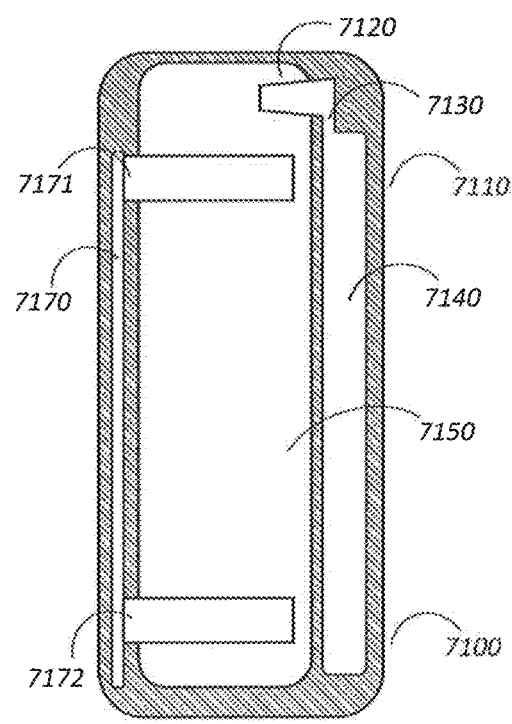
Figure 22I:
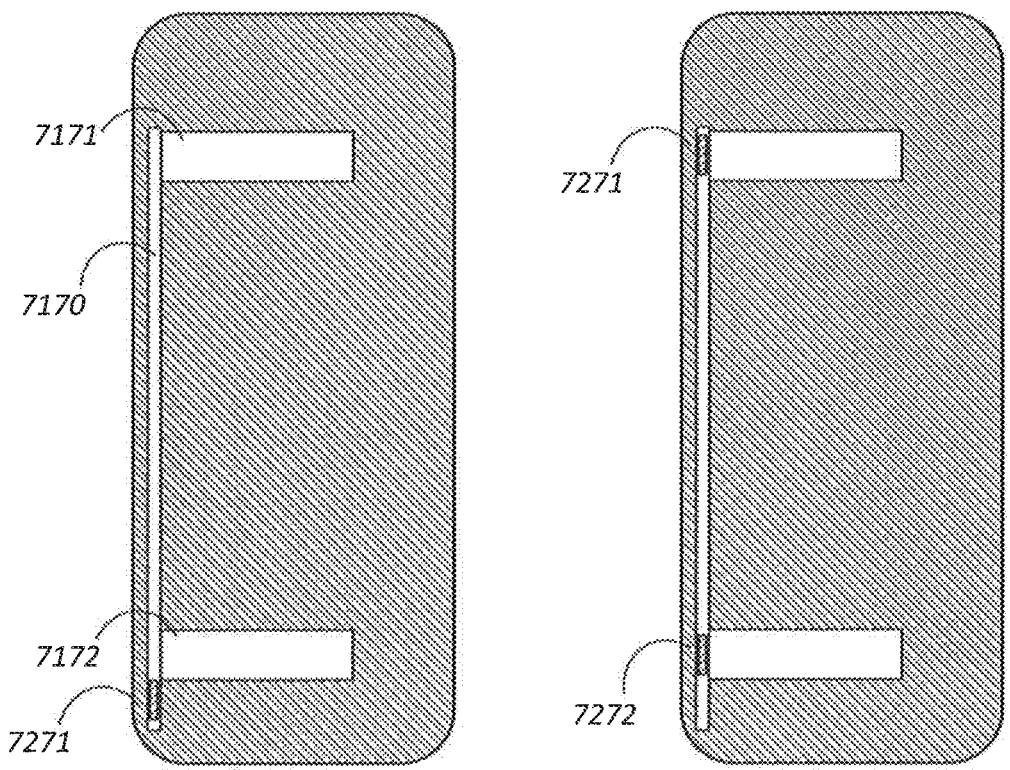
Figure 22H:
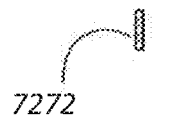
Figures 22J, 22K:
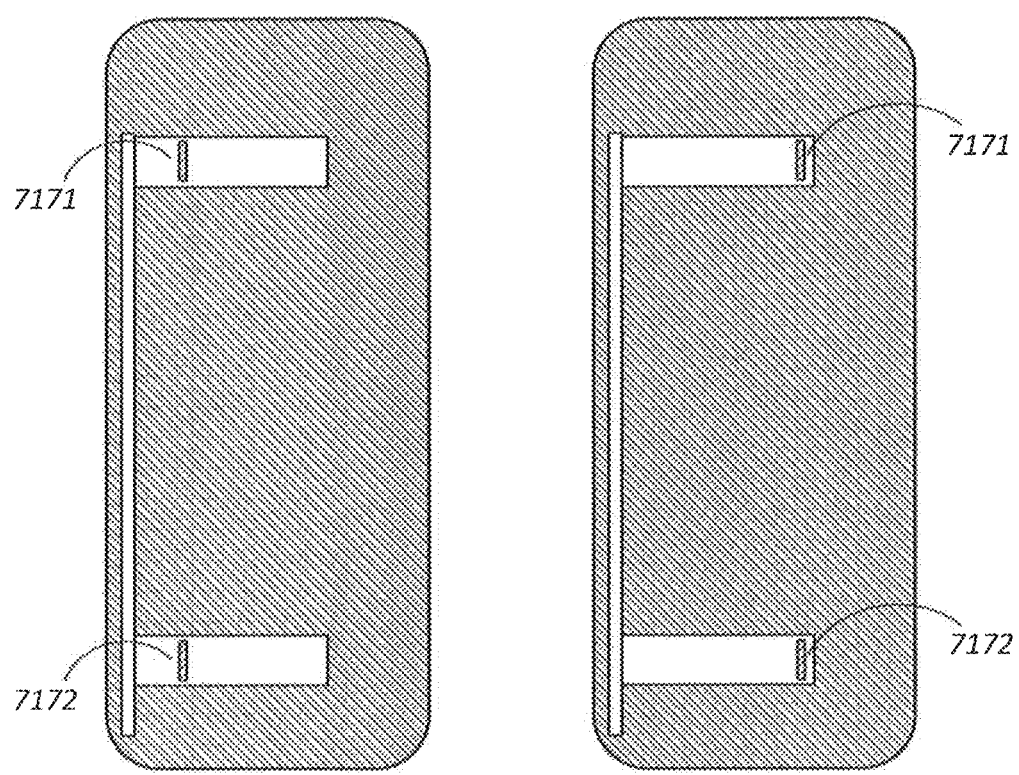
Figures 22L, 22M:
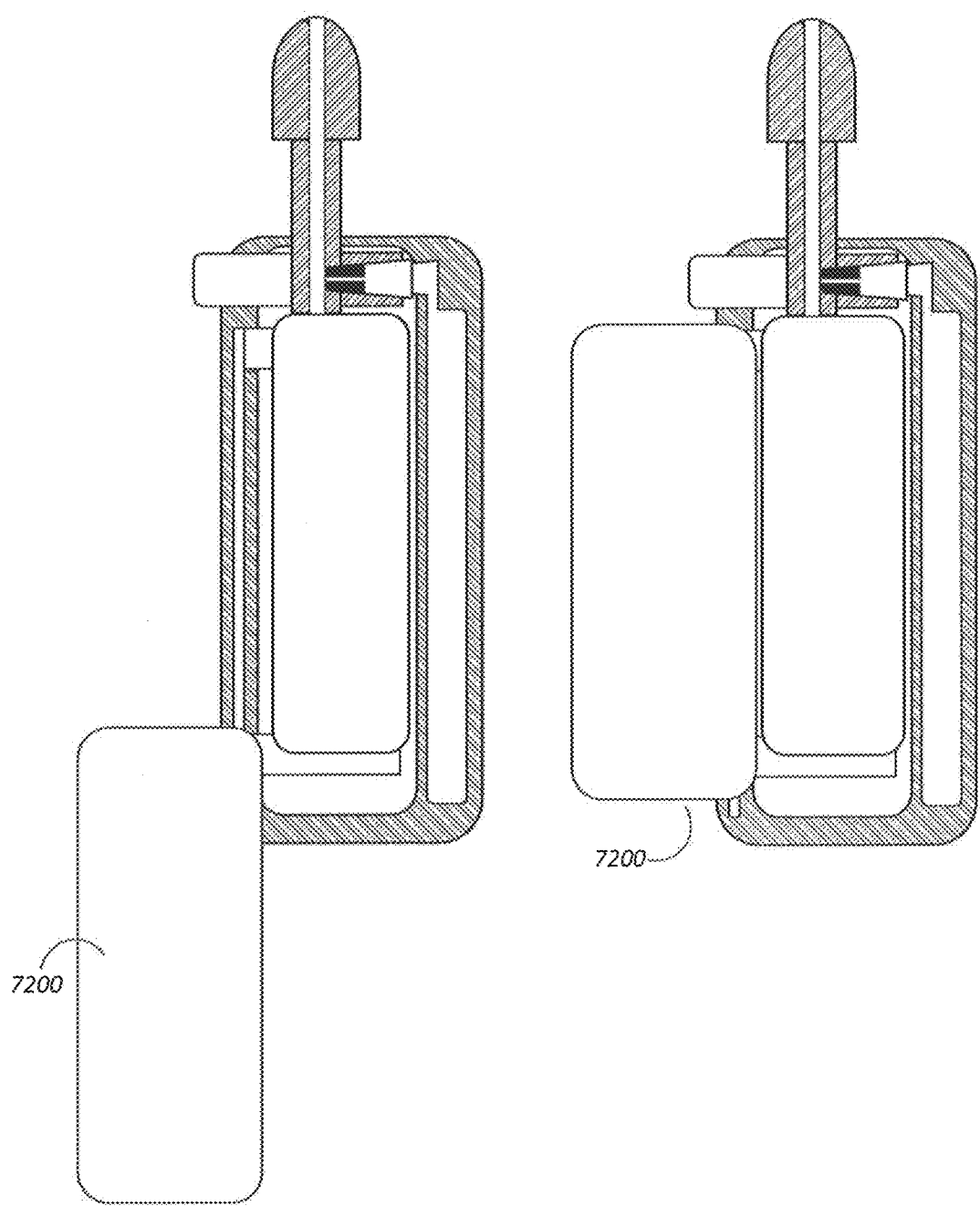
Figure 22N:
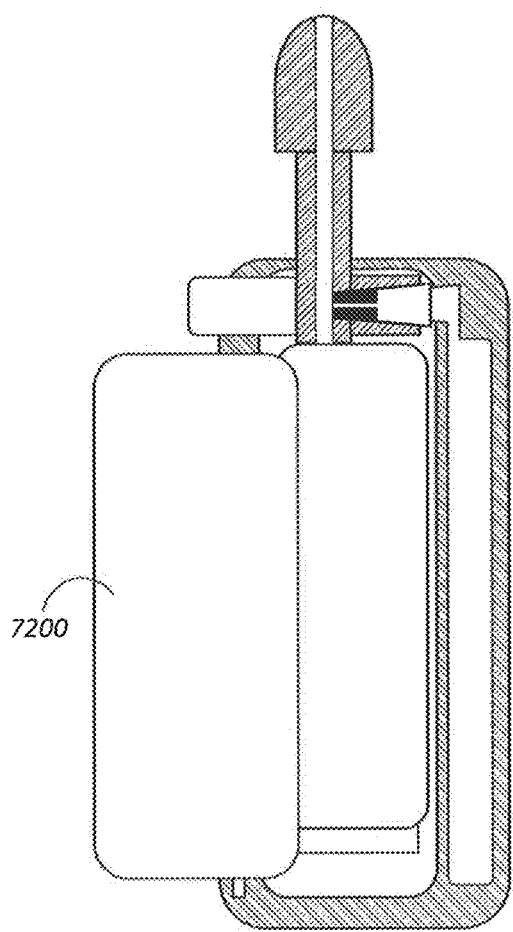
Figure 22O:
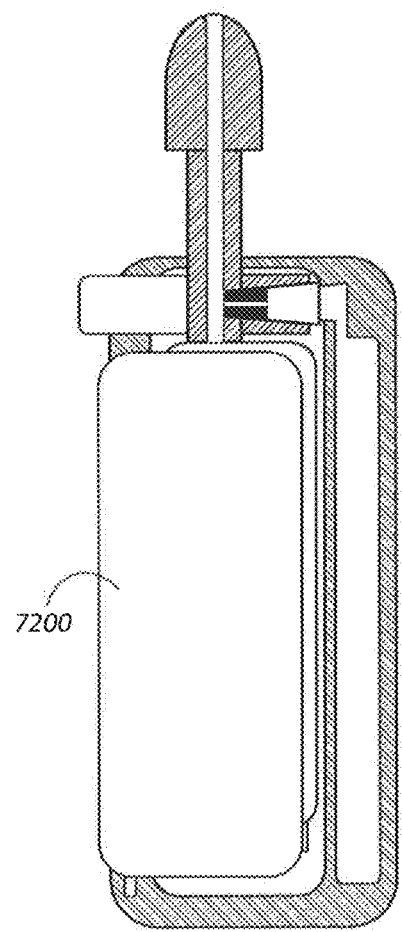

FIGS. 22A through 22O relate in detail to a Fluid Introduction and Retention Unit utilizing a fluid cartridge.

FIGS. 22A and 22F illustrate a preferred embodiment of a fluid cartridge 6000 which can be sold or otherwise provided to the user empty, completely pre-filled or partially pre-filled with liquid. The complete or partial pre-filling of cartridges provides important benefits. Pre-filling is more convenient to the user as it eliminates the step of the user sterilizing and then mixing saline or other medicinal solution. This inconvenience often results in users inadequately sterilizing the fluid. As a result, it has been reported that at least one neti pot user has died from an *Naegleria fowleri* amoebic brain infection from using inadequately sterilized water used to rinse his nasal passages. Partially or completely pre-filled cartridges 6000 can be sterilized at the factory, minimizing the possibility of fluid contamination. The unfilled cartridges can, for example, be sterilized by ETO, and then sterilized fluid can be added. Alternatively, the pre-filled cartridges can be sterilized using standard gamma radiation techniques. Cartridges 6000 may be pre-filled with precisely measured amounts of medication and/or mixtures of medications. An optional elastomeric septum 6120 may be incorporated through which additional medicinal materials can be injected using a hypodermic needle. Cartridges 6000 may be completely disposable and are designed to be compatible with one-time use.

A cartridge nozzle 6010 is secured atop a cartridge neck 6070. A cartridge half-ring 6060, a cartridge tab 6020, and a cartridge Luer housing 6080 are affixed to the side of cartridge neck 6070. Within Luer housing 6080 is a female Luer connector 6040. Further inside Luer housing 6080 is a one-way valve 6030 employed to prevent the inadvertent outward flow of the fluid. Nozzle 6010, neck 6070, half-ring 6060, tab 6020, and Luer housing 6080 are typically rigid or semi-rigid. A cartridge bag 6050 contains at least the bulk of the fluid and is typically made from a very pliable material such as medical grade polyethylene film.

A cartridge nozzle cap 6090 can be a shrink wrapped covering over cartridge nozzle 6010. Nozzle cap 6090 keeps nozzle 6010 sterile and holds a cartridge nozzle plug 6100 tightly in cartridge nozzle opening 6110 to prevent leakage therefrom. Nozzle plug 6100 can be an elastomeric material.

FIGS. 22B through 22E and 22G through 22O illustrate a preferred embodiment of a Fluid Introduction and Retention Unit 7000 that is compatible with fluid cartridge 6000. The two primary elements of Fluid Introduction and Retention Unit 7000 are Unit body 7100 and Unit plunger 7200. Unit body 7100 has a body chamber 7150 for housing a cartridge 6000. In each of the two internal side walls of body chamber 7150 are plunger grooves 7171 near the top of the body 7100 and plunger grooves 7172 near the bottom of the body 7100. A male Luer connector 7120 leads to a channel 7130 which leads to a region 7140 which is a space containing an air pump and the batteries that drive that air pump. The air pump can be a diaphragm pump such as those used to keep caught fish alive while bringing them home.

FIGS. 22B and 22G illustrate Unit body 7100 when cartridge 6000 is not installed. Cartridge 6000 can be grasped by a cartridge tab 6020 and then inserted into Unit 7100 such that: cartridge bag 6050 goes into Unit body chamber 7150; cartridge neck 6070 rests in Unit body neck support 7190; and cartridge half-ring 6060 rests in Unit body half-ring support 7180. This positioning aligns cartridge female Luer connector 6040 with male Luer connector 7120. The fit of cartridge half-ring 6060 in half-ring support 7180 is sufficiently tight to hold female Luer connector 6040 to Unit body male Luer connector 7120 tightly enough to prevent any leaks and keep cartridge 6000 from moving inadvertently or unexpectedly. This tight fit is achieved by pressure applied at that interface by the user's grasp on cartridge tab 6020. FIGS. 22C, 22H and 22L illustrate cartridge 6000 as newly installed in Unit body 7100.

Once cartridge 6000 is installed in Unit body 7100, Unit plunger 7200 is slid over Unit body chamber 7150. Pressing upward on plunger 7200 causes plunger tabs 7271 and 7272 to slide in vertical grooves 7170 until plunger tabs 7271 can enter body grooves 7171, and plunger tabs 7272 can enter horizontal body grooves 7172 as illustrated in FIGS. 22D, 22E, 22I, and 22M. Unit 7000, including cartridge 6000, is ready for use once cartridge nozzle cap 6090 is removed (which pulls out the affixed cartridge nozzle plug 6100 from cartridge nozzle opening 6110).

As illustrated in FIGS. 22J, 22K and 22M through 22O, squeezing the plunger 7200 into body 7100 causes cartridge bag 6050 to be squeezed and the fluid to be discharged through nozzle opening 6110 and into the user's nose. When ready, the user can press air pump switch 7195 to turn on the air pump.

Just as cartridge tab 6020 is used to install cartridge 6000 into Unit body 7100, cartridge tab 6020 is grasped to remove cartridge 6000.

Alternatively, tip member 310 and syringe 360 combined can be disposable and pre-filled with sterilized fluids, again with a cartridge nozzle cap.

Another benefit of the use of cartridges 6000 and Fluid Introduction and Retention Unit 7000 is that the amount of fluid to be delivered is precisely controlled. The volume of that cartridge can be chosen to fill or nearly fill the sinus cavity and sinuses.

The invention as described herein includes several advantages and features, as described, and further includes, but is not limited to, the capability of:

providing prolonged exposure of one or more of nasal and/or sinus membranes, including the olfactory cleft and/or the olfactory bulb, to an irrigation or medicament liquid;

supporting a liquid column within a person's nasal cavity to thereby effect prolonged residence time of the liquid in the nasal cavity;

measuring angular displacement of a person's head to permit delivery of irrigation or medicament liquid to specified target cavities and structures in a user's head;

creating turbulence in a liquid being delivered to nasal passages and sinuses to enhance nasal bathing and irrigation; and providing cartridges of nasal bathing and irrigation fluid for convenient and safe use with the system of the invention.

The head orientation unit embodiments described herein are merely preferred examples of units having any attachment member that is temporarily affixed to the head of a person and any two dimensional angular monitoring and display device that is secured to and moves with the attachment member and the person's head to provide a display of the angular position of the head and permit the person to orient his/her head in predetermined positions and sequentially move his/her head along paths of such positions. It is to be understood that any structures or methods providing these functions are considered to be included within the scope of the present invention. As described herein, the primary use of such head orientation units is to permit bathing and/or medication liquid to be properly administered to nasal, sinus and other structures in the person's head via the person's nostrils. However, it is to be understood that such head orientation units, to the extent that they function for other applications, are considered to be included within the scope of the present invention.

It is also to be understood that the several embodiments of Fluid Introduction and Retention Units illustrated and described herein are merely exemplary of a wide variety of liquid supply means and that any units capable of performing the functions ascribed herein to such units can be utilized in the systems and methods of the present invention. Likewise, it is to be understood that the system of the invention may employ several alternative types of Fluid Agitation Units for creating turbulence in the bath liquid whereby the turbulence is introduced by pressurized gas, mechanical agitation, or electrical discharge. Further the disposable cartridges illustrated and described herein are merely exemplary and that any cartridges capable of performing the functions ascribed herein can be utilized in the systems and methods of the present invention.

Furthermore, it should be understood that the expression "liquid supply means" as used in the claims includes, for example, any one of the following described features of the present invention: (a) syringe 260, 360 and tip member 210, 310 as described herein and illustrated in FIGS. 2A-2B and 3A; and (b) fluid cartridge 6000 including cartridge bag 6050 and cartridge nozzle 6010 as described herein and illustrated in FIGS. 22A and 22F.

Also, it should be understood that the expression "turbulence inducing means" as used in the claims includes, for example, any one of the following described features of the present invention: (a) fluid agitation unit 370 including (i) hand pump 390 as described herein and illustrated in FIG. 3C, (ii) pump 3000 with flow limiter 3062 as described herein and illustrated in FIG. 11, (iii) water-pressured powered, turbine air pump 3200 with flow limiter 3262 as described herein and illustrated in FIG. 12, (iv) battery-powered air pump 3490 as described herein and illustrated in FIG. 13C, (v) pressurized $CO_2$ cartridges as described herein, and (vi) pressurized gas generated from a chemical reaction as described herein; (b) nozzles 4400 as described herein and illustrated in FIGS. 14C-14F; (c) mechanically induced turbulence nozzles 4600, 4700 including mechanical drive unit 4770 as described herein and illustrated in FIGS. 15A-15B, or turbulence propeller 4622, 4722 as described herein and illustrated in FIGS. 16A-16B; and (d) actuator button 5244 and associated structure for producing repetitive fluid flow reversal into and out of the user's nostrils as described herein and illustrated in FIGS. 19C-19D.

Further, it should be understood that the expression "means for applying pressure" as used in the claims includes, for example, the following described feature of the present invention: the unit plunger 7200 as described herein and illustrated in FIGS. 22B-22E.

In addition, it should be understood that the expression "bubble level unit" as used in the claims includes, for example, the following described features of the present invention: (a) the bubble level device 1440 as described herein and illustrated in FIGS. 4A-4D; and (b) the bubble level device 1660 as described herein and illustrated in FIGS. 6A-6F.

Having described preferred embodiments of new and improved system and method for improved irrigation and medication of the sinus, nasal and other internal structures in the head of a person, and various novel components thereof, it is believed that other modifications, variations and changes will be suggested to those skilled in the art in view of the teachings set forth herein. It is therefore to be understood that all such variations, modifications and changes are believed to fall within the scope of the present invention as defined by the appended claims. Although specific terms are employed herein, they are used in a generic and descriptive sense only and not for purposes of limitation.

What is claimed is:

1. A system for delivering a liquid via a user's nostrils and maintaining prolonged exposure of the liquid to one or more head structures in a user's nasal cavity and sinuses when the user is facing downward, said system comprising:
    a bubble level unit configured to move with a user's head for providing an indication of an angular orientation of the user's head;
    a liquid supply means for delivering the liquid through the user's nostrils to the one or more head structures, the one or more head structures determined by the indication of said angular orientation of the user's head;
    the indication of the angular orientation of the user's head provided by indicia on the bubble level unit, the indicia designating the one or more head structures for selective introduction and retention of the liquid from the liquid supply means; and
    turbulence inducing means for creating turbulent flow in the liquid being delivered to the one or more structures.

2. The system of claim 1, wherein said bubble level unit includes:
    a gas bubble configured to assume a position that is a function of the angular orientation of the user's head; and
    the indicia demarking predetermined angular orientations of the user's head when aligned with the gas bubble.

3. The system of claim 1, wherein said turbulence inducing means consists of a selected one of an aeration device, a mechanical agitator, a bladed propeller, a flow rate modifier and a flow direction modifier.

4. The system of claim 3,
    wherein the turbulence inducing means is selected to be the aeration device; and
    wherein the aeration device is a fluid agitation unit consisting of one of a hand pump, a powered air pump, a pressurized CO2 cartridge, and a pressurized gas generated from a chemical reaction of effervescent tablets, granules and/or powder added to the liquid.

5. The system of claim 3,
    wherein the turbulence inducing means is selected to be the mechanical agitator; and
    wherein the mechanical agitator is a mechanical drive unit coupled to a mechanically induced turbulence nozzle.

6. The system of claim 3,
    wherein the turbulence inducing means is selected to be the bladed propeller; and
    wherein the bladed propeller is secured within a turbulence chamber of a mechanically induced turbulence nozzle.

7. The system of claim 3,
    wherein the turbulence inducing means is selected to be the flow rate modifier; and
    wherein the flow rate modifier is a water flow restrictor.

8. The system of claim 3,
    wherein the turbulence inducing means is selected to be the flow direction modifier; and
    wherein the flow direction modifier includes an actuator which, upon being repetitively pressed and released by the user, reverses the flow of liquid into and out of the user's nostril.

9. The system of claim 1, wherein said liquid supply means includes a syringe and a tip member for directing outflow of the liquid from said syringe, said tip member being configured to be partially inserted in the user's nostrils in pressure sealing relation.

10. The system of claim 1, wherein said liquid supply means includes:

a pliable cartridge containing said liquid;

a housing for receiving said cartridge; and means for applying pressure to said cartridge in said housing to force said liquid from the housing.

11. The system of claim 1, wherein said bubble level unit includes a gas bubble in a liquid confined to a portion of a spherical shell.

12. The system of claim 11, wherein the spherical shell is defined by a truncated spherical outer shell wall having the indicia thereon, the indicia corresponding to predetermined angular orientations of the user's head and wherein alignment of the gas bubble to each indicium of the indicia corresponds to a predetermined angular orientation of the user's head that is optimal for introduction and retention of liquid to the one or more head structures.

13. The system of claim 11, wherein said spherical shell is defined by a truncated spherical outer shell wall and a truncated spherical inner shell wall;

wherein the inner and outer shell walls are spaced apart; and wherein the gas bubble and liquid are confined between the inner and outer shell walls.

14. The system of claim 12, wherein the gas bubble has a diameter;

wherein the indicia are circles each having a diameter similar in size to the diameter of the air bubble; and wherein alignment of the gas bubble to each indicium of the indicia corresponds to a predetermined angular orientation of the user's head that is optimal for the introduction and retention of the liquid to, or into, one or more of the head structures in the user's nasal cavity and sinuses.

15. The system of claim 14, wherein each indicium has a label designating a head structure of the one or more head structures for which its orientation is optimized.

* * * * *